(12) United States Patent
Hirshberg

(10) Patent No.: US 11,394,319 B2
(45) Date of Patent: Jul. 19, 2022

(54) PIERCING APPARATUS AND A METHOD OF FABRICATING THEREOF

(71) Applicant: David Hirshberg, Haifa (IL)

(72) Inventor: David Hirshberg, Haifa (IL)

( * ) Notice: Subject to any disclaimer, the term of this patent is extended or adjusted under 35 U.S.C. 154(b) by 109 days.

(21) Appl. No.: 16/805,886

(22) Filed: Mar. 2, 2020

(65) Prior Publication Data
US 2021/0273585 A1    Sep. 2, 2021

Related U.S. Application Data

(63) Continuation-in-part of application No. 15/296,068, filed on Oct. 18, 2016, now Pat. No. 10,625,029, which is a continuation-in-part of application No. 14/326,537, filed on Jul. 9, 2014, now Pat. No. 9,931,478, which is a continuation-in-part of
(Continued)

(51) Int. Cl.
| | |
|---|---|
| *H02N 2/02* | (2006.01) |
| *H02N 2/00* | (2006.01) |
| *H02N 2/06* | (2006.01) |
| *H02N 2/10* | (2006.01) |
| *H02N 2/14* | (2006.01) |
| *G11B 19/20* | (2006.01) |
| *A61M 37/00* | (2006.01) |
| *A61M 5/158* | (2006.01) |

(52) U.S. Cl.
CPC .......... *H02N 2/023* (2013.01); *H02N 2/0015* (2013.01); *H02N 2/062* (2013.01); *H02N 2/101* (2013.01); *H02N 2/142* (2013.01); *H02N 2/22* (2013.01); *A61M 5/158* (2013.01); *A61M 37/0015* (2013.01); *G11B 19/2009* (2013.01)

(58) Field of Classification Search
CPC ...... H02N 2/023; H02N 2/0015; H02N 2/062; H02N 2/101; H02N 2/142; H02N 2/22; A61M 5/158; A61M 37/0015; G11B 19/2009
See application file for complete search history.

(56) References Cited

U.S. PATENT DOCUMENTS

| | | | | |
|---|---|---|---|---|
| 2003/0230798 A1* | 12/2003 | Lin | ........................ | B81B 7/0064 257/E23.114 |
| 2012/0209303 A1* | 8/2012 | Frankhouser | ...... | A61B 17/3476 606/169 |

(Continued)

*Primary Examiner* — Emily P Pham

(57) ABSTRACT

An apparatus and a method of fabricating an apparatus for piercing an object, the apparatus comprises: a substrate; one or more needles; one or more anchors and one or more piezoelectric actuators. The method comprises the steps of deposit sacrificial layer over the substrate; deposit conducting layer over the sacrificial layer; deposit piezoelectric layer over the conducting layer; etch a geometry of the one or more piezoelectric actuators using a first mask created by lithography process; deposit the one or more needle and one or more anchors using a second mask created by lithography process and a lift-off process; etch the sacrificial layer under the needle and the one or more piezoelectric actuators, wherein the anchors are configured to connect the substrate to the piezoelectric actuators and the one or more piezoelectric actuators are configured to expand, contract or bend, and form holding arms that are configured to move the one or more needles.

20 Claims, 17 Drawing Sheets

Related U.S. Application Data application No. 13/426,684, filed on Mar. 22, 2012, now Pat. No. 9,409,006.

(60) Provisional application No. 61/473,779, filed on Apr. 10, 2011.

(56) References Cited

U.S. PATENT DOCUMENTS

| | | | |
|---|---|---|---|
| 2014/0323837 A1* | 10/2014 | Hirshberg | A61B 5/6848 604/117 |
| 2017/0258489 A1* | 9/2017 | Galili | A61M 39/02 |
| 2018/0287047 A1* | 10/2018 | Rinaldi | H01L 41/107 |
| 2019/0344257 A1* | 11/2019 | Naing | A61L 2/07 |

* cited by examiner

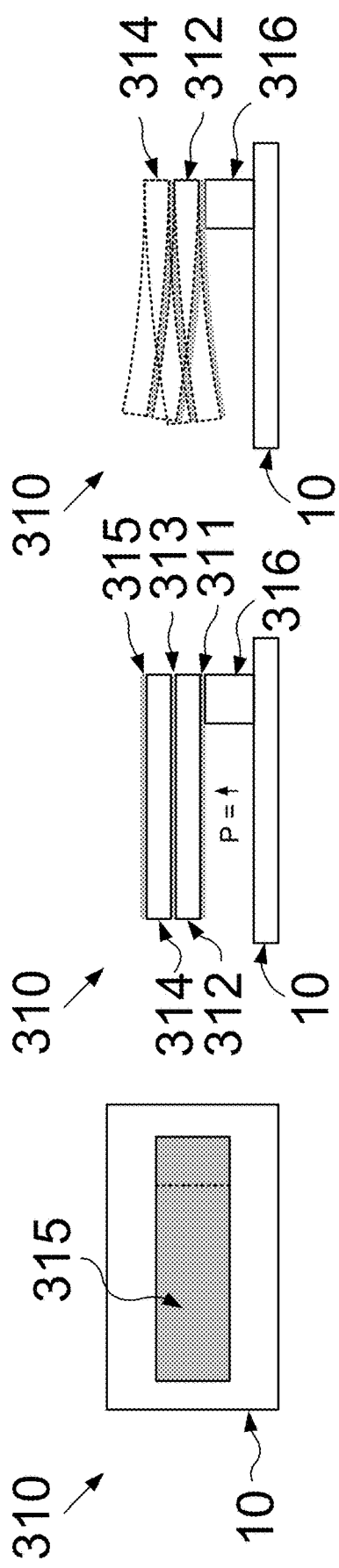
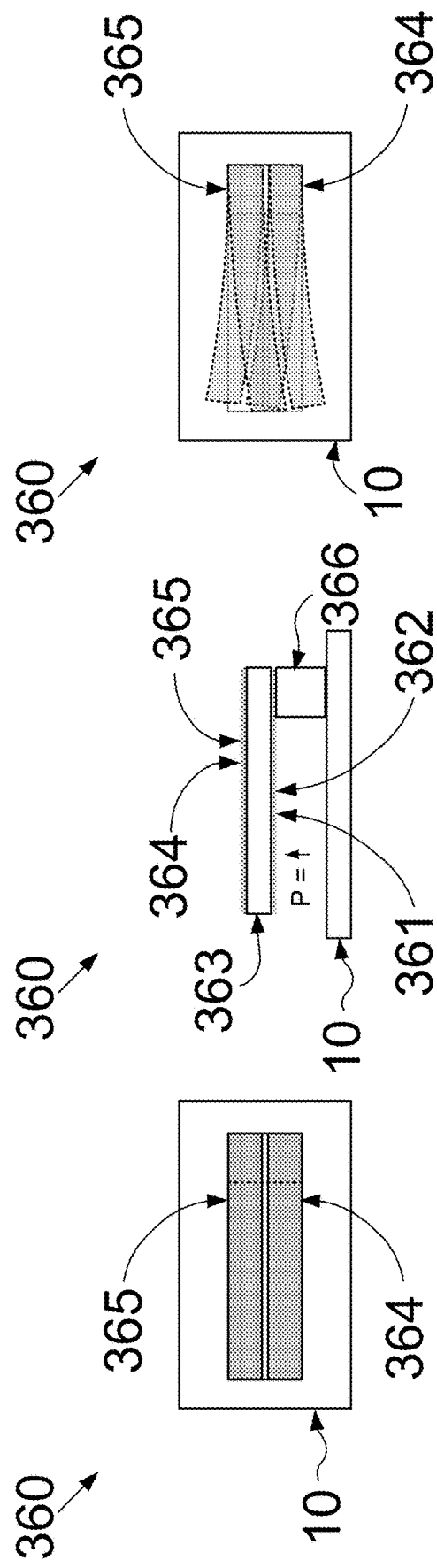

Bending Movement

Elliptic Movement

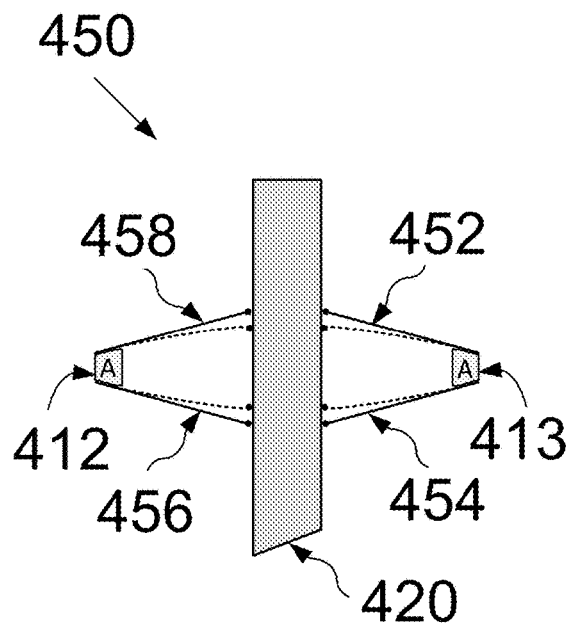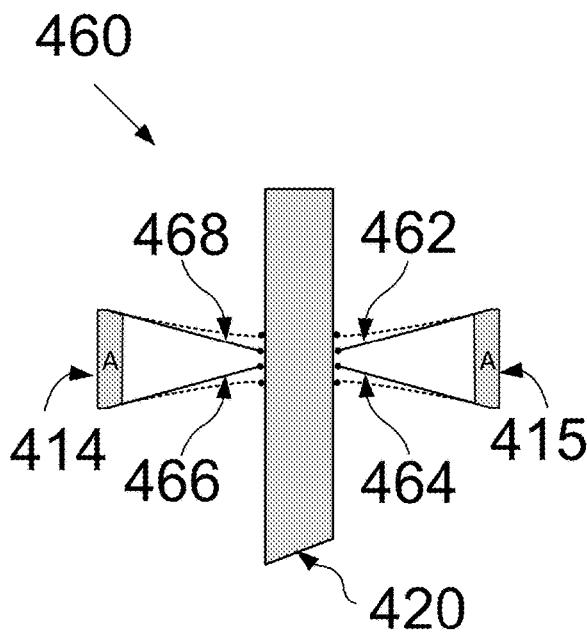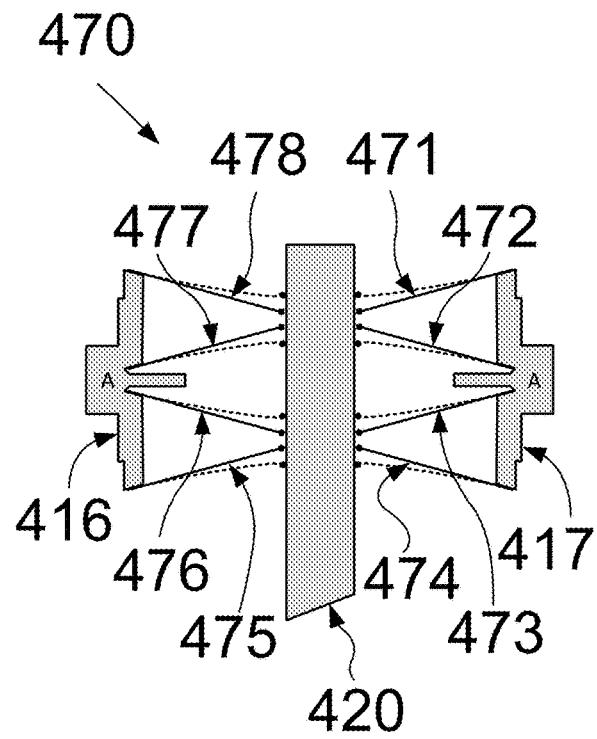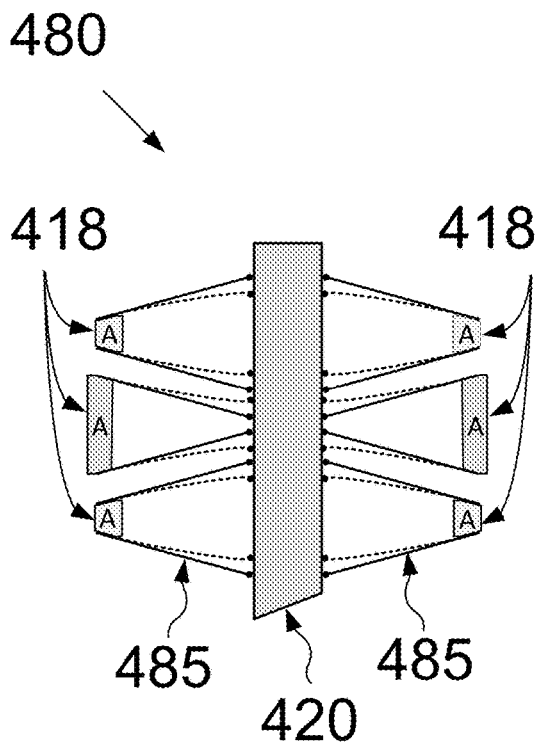

PIERCING APPARATUS AND A METHOD OF FABRICATING THEREOF

RELATED APPLICATION/S

This application is a continuation-in-part (CIP) of U.S. patent application Ser. No. 15/296,068 filed Oct. 18, 2016, which is a continuation-in-part (CIP) of U.S. patent application Ser. No. 14/326,537 filed Jul. 9, 2014, which is a continuation-in-part (CIP) of U.S. patent application Ser. No. 13/426,684 filed Mar. 22, 2012, which claims priority under 35 U.S.C. § 119(e) of U.S. provisional patent application 61/473,779 filed Apr. 10, 2011. The contents of the above documents are incorporated by reference as if fully set forth herein.

FIELD AND BACKGROUND OF THE INVENTION

The present invention, in some embodiments thereof, relates to needles that penetrate objects or organs, and more particularly, but not exclusively, to a system with actuators for the needles.

Needles are thin objects, optionally hollow, with sharp tip in its end to allow penetration into or passage through an object or organ. Needles have many usages. It is used in sewing, in crafting for making small holes, in research, especially in biology, and in medicine. In medicine, needles are used to inject fluid into or extract fluid from the body as well as in other treatments, such as, stimulating treatments, like acupuncture, or for monitoring treatment, like brain activity probing and monitoring.

One of the most popular type of needle is a hypodermic needle that is configured to penetrate the skin. In some applications, the needle is used to inject fluid to or extracting fluid from the intercellular fluid and in other applications extracting blood or injection drugs to or from a blood vassal.

Typically today, hypodermic needle is made of stainless-steel and the diameter of the needle is between 0.2 mm, i.e., 200 micron, to 5 mm. In recent years, needles with a thin diameter are made also from other materials, such as silicon. These needles are produced using semiconductors manufacturing processes and fabrication facilities.

SUMMARY OF THE INVENTION

According to an aspect of some embodiments of the present invention there is provided needle system or piercing apparatus that penetrates objects or organs, in general and more particularly, but not exclusively, needle system that is used for medical treatments for humans.

According to an aspect of some embodiments of the present invention there is provided an apparatus for piercing an object comprising:
(a) a semiconductor die; (b) one or more needles; and (c) one or more actuators, wherein the actuators are attached to the die substrate and to the needles, the actuators move the needles relative to the die plan, and the needles are configured to pierce the object.

According to some embodiments of the invention the one or more needles are configured to slide over the die plane.

According to some embodiments of the invention the one or more needles moves out of die plane.

According to an aspect of some embodiments of the present invention there is provided a needle system for penetrating to or passing thought an object or an organ comprising: (a) a semiconductor die; (b) one or more needles, wherein the needles slide over the plane of the die; (c) one or more actuators that move the needles relative to the die plane; and (d) one or more actuator drivers controlled by a controller; wherein the controller instructs the needle to penetrate into or to pass through and/or retract from the object or organ.

According to some embodiments of the invention, the one or more the needles are inserted none perpendicularly to anchoring the needle system into the object or organ.

According to some embodiments of the invention, the needle system comprises plurality of semiconductor dies.

According to some embodiments of the invention, a first semiconductor dies is assembled perpendicular to a second semiconductor dies and the second semiconductor dies comprises vias which the needles are passing through those vias.

According to some embodiments of the invention, the needle movement mechanism comprises a ratchet mechanism to restrict the direction of movement and lock the needle movement between movements' steps.

According to some embodiments of the invention, the actuators are electromagnetic or electrostatic or piezoelectric actuators.

According to some embodiments of the invention, the needle has mechanical support to hold the needle and to allow sliding only to a desired direction.

According to some embodiments of the invention, the needle system has friction reduction mechanism to reduce the needle friction during sliding over the die.

According to some embodiments of the invention, the needle is hollow.

According to some embodiments of the invention, the needle system is used for drug delivery or blood extraction or blood analysis or glucose measurements or blood measurements or nerve system stimulus treatment or hair removal or skin lesions removal.

According to an aspect of some embodiments of the present invention there is provided a method of fabricating an apparatus for piercing an object, the apparatus comprises: a substrate; one or more needles; one or more anchors and one or more piezoelectric actuators, the method comprises the steps of: deposit sacrificial layer over the substrate; deposit conducting layer over the sacrificial layer; deposit piezoelectric layer over the conducting layer; etch a geometry of the one or more piezoelectric actuators using a first mask created by lithography process; deposit the one or more needle and one or more anchors using a second mask created by lithography process and a lift-off process; etch the sacrificial layer under the needle and the one or more piezoelectric actuators, wherein the anchors are configured to connect the substrate to the piezoelectric actuators and the one or more piezoelectric actuators are configured to move the one or more needles.

According to some embodiments of the invention, the method further comprises a step of etching a through-chip via to enable needle out-of-plane movement through the substrate According to some embodiments of the invention, the method further comprises a step of etching a through-chip via to be filled with conducting materials and to be configured to provide a connection with another die using wafer bonding.

According to some embodiments of the invention, the method further comprises a step of depositing tiles of piezoelectric materials interleaved with tiles of conducting materials using two masks lithography and liftoff processes.

According to some embodiments of the invention, the method further comprises a step of depositing multilayers of piezoelectric materials interleaved with layers of conducting materials.

According to some embodiments of the invention, the apparatus for piercing an object fabricated in accordance with the method described hereinabove.

According to an aspect of some embodiments of the present invention there is provided a method of fabricating an apparatus for piercing an object, the apparatus comprises: a substrate; one or more needles; one or more anchors and one or more piezoelectric actuators, The method comprises the steps of: deposit conducting layer over the substrate; deposit piezoelectric layer over the conducting layer; etch a geometry of the one or more piezoelectric actuator using a first mask created by lithography process; deposit the one or more needle and one or more anchors using a second mask created by lithography process and a lift-off process; etch the top surface of the substrate under the needle and the one or more piezoelectric actuators using a two stage SCREAM etching process comprising: first, vertical anisotropic dry etching of pattern of pores, and second, horizontal extension of the pores etching using wet or gas etching, wherein the anchors are configured to connect the substrate to the piezoelectric actuators and the one or more piezoelectric actuators are configured to move the one or more needles.

According to some embodiments of the invention, the method further comprises a step of etching a through-chip via to enable needle out-of-plane movement through the substrate According to some embodiments of the invention, the method further comprises a step of etching a through-chip via to be filled with conducting materials and to be configured to provide a connection with another die using wafer bonding.

According to some embodiments of the invention, the method further comprises a step of depositing tiles of piezoelectric materials interleaved with tiles of conducting materials using two masks lithography and liftoff processes.

According to some embodiments of the invention, the method further comprises a step of depositing multilayers of piezoelectric materials interleaved with layers of conducting materials.

According to some embodiments of the invention, the apparatus for piercing an object fabricated in accordance with the method described hereinabove.

According to an aspect of some embodiments of the present invention there is provided an apparatus for piercing an object comprising: (a) one or more needles; and (b) one or more piezoelectric actuators comprising a at least one of or any combination of one or more piezoelectric stack actuators and one or more piezoelectric cantilever actuators, wherein: the one or more piezoelectric actuators form a plurality of arms that are configured to grip the one or more needles; the needles are configured to pierce the object; the piezoelectric actuators are configured to expand, contract or bend; the arms are configured to dynamically hold or release the grip from the needles by expanding, contracting or bending some of the plurality of the piezoelectric actuators; and when some of the arms hold the needles, these holding arms are configured to move the one or more needles by expanding, contracting or bending some of the plurality of the piezoelectric actuators.

According to some embodiments of the invention, the apparatus further comprising a one or more drivers configured to activate the one or more piezoelectric actuators and a controller configured to control the drivers.

According to some embodiments of the invention, the apparatus comprising first four piezoelectric stack actuators configured to grip any of the one or more needles and a second four piezoelectric stack actuators configured to move the first four piezoelectric stack actuators.

According to some embodiments of the invention, the piezoelectric cantilever actuator performs at least one of bending movement or elliptic movement.

According to some embodiments of the invention, the one or more needles have mechanical support to hold the needle and to allow sliding only to a desired direction.

According to some embodiments of the invention, the object is a human organ and the one or more needles are used for hypodermal treatment.

According to some embodiments of the invention, the object is an article of manufacturing and the system is used for manipulating or piercing the object during the process of the manufacturing.

According to some embodiments of the invention, the object is a lab object under test or a biological organ and the system is used for testing or measuring or manipulating the lab object under test or the biological organ.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, some hardware for performing selected tasks according to embodiments of the invention, if not explicitly specified, could be implemented as a chip or a circuit. As software, selected tasks according to embodiments of the invention could be implemented as a plurality of software instructions being executed by a computer or controller using any suitable operating system. In an exemplary embodiment of the invention, one or more tasks according to exemplary embodiments of method and/or system as described herein are performed by a processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a top view of the piercing apparatus in close, i.e., initial, position;

FIG. 1B is a cross section of the piercing apparatus across line A-A indicated in FIG. 1A;

FIG. 1C is a top view of the piercing apparatus in fully open position;

FIG. 3A is a top view of the die;

FIG. 3B is a cross-sectional view of the die view across line C-C indicated in FIG. 3A when the needle is in initial close state;

FIG. 3C is a cross-sectional view of the die view across line C-C indicated in FIG. 3A when the needle is in open penetrated state;

FIG. 5A is a top view of the die;

FIG. 5B is a cross section side view across line A-A indicated in FIG. 5A;

FIG. 7A is an isometric view;

FIG. 7B is a side view;

FIG. 8A is a zoom-in top view the step motor;

FIG. 8B is a top view of the full die;

FIG. 9A is a top view of the die;

FIG. 9B is a cross section side view across line C-C indicated in FIG. 9A;

FIG. 9C is a cross section side view across line C-C indicated in FIG. 9A of a modified version comprising modified piezoelectric stack actuators;

FIG. 9D is a top view of modified version comprising a 3D needle array on the die;

FIG. 10A-FIG. 10F are illustrations of piezoelectric cantilevers actuators in accordance with the present invention;

FIG. 10A is a top view out-of-plane (perpendicular to substrate plane) bending cantilever;

FIG. 10B is a side view of the out-of-plane bending cantilever of FIG. 10A;

FIG. 10C is a side view of the bending operation of the out-of-plane bending cantilever of FIG. 10A;

FIG. 10D is a top view in-plane (parallel to substrate plane) bending cantilever;

FIG. 10E is a side view of the in-plane bending cantilever of FIG. 10D;

FIG. 10F is a top view of the bending operation of the in-plane bending cantilever of FIG. 10D;

FIG. 11A is a top view of bending movement relative to a needle;

FIG. 11B is a top view of elliptic movement relative to a needle;

FIG. 12A-FIG. 12D are illustrations of in-plane needle movement step motors comprising piezoelectric cantilever actuators in accordance with some embodiments of the present invention;

FIG. 12A is a top view of a four cantilever embodiment;

FIG. 12B is a top view of another four cantilever embodiment;

FIG. 12C is a top view of a eight cantilever embodiment;

FIG. 12D is a top view of a twelve cantilever embodiment;

FIG. 13A is a top view of the step motor;

FIG. 13B is a cross section side view across line F-F indicated in FIG. 13A;

FIG. 13C is a cross section side view across line G-G indicated in FIG. 13A;

FIG. 15A is a top view of the fabricated apparatus;

FIG. 15B is cross section side view across line H-H indicated in FIG. 15A of a desired final fabricated apparatus.

FIG. 15C-FIG. 15K are cross section side view across line H-H indicated in FIG. 15A of the fabricated apparatus after the first to ninth stages respectively; and FIG. 15L is a cross section side view across line H-H indicated in FIG. 15A of the fabricated apparatus after the last stage in an alternative process.

DESCRIPTION OF SPECIFIC EMBODIMENTS OF THE INVENTION

Figure 1A:
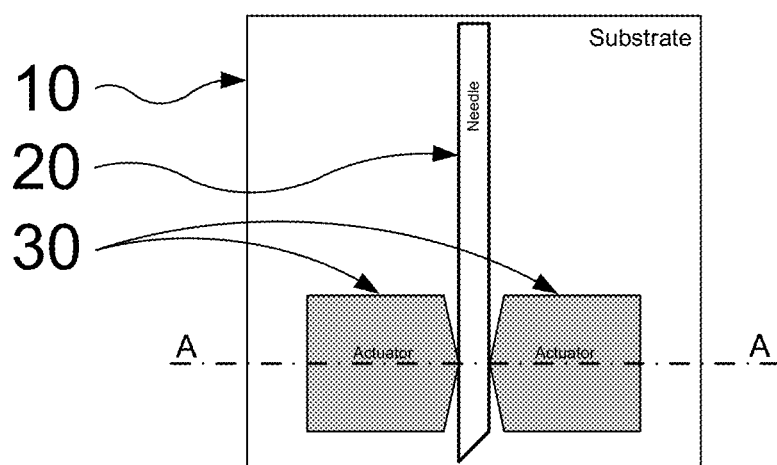
FIG. 1A-FIG. 1C are illustrations of an exemplary embodiment of simplified construction and operation of the present invention piercing apparatus.

The present invention, in some embodiments thereof, relates to piercing apparatus that use needles to penetrate objects or organs, and more particularly, but not exclusively, to needles that are used for medical treatments for humans.

The current technology of piercing apparatus does not couple between the needle fabrication and the needle mechanical subsystem that is responsible for the insertion and retraction of the needles to the target object or organ. Currently there are two prominent ways of controlling penetration and retraction of the needle: manually or spring activated. In manual activation, the doctor, nurse or the patient himself sticks to and retracts the needle with his hand. Such an operation has its limitations both in accuracy and in the speed of operation. Spring operated activation uses the mechanical energy stored in a string to inject or retract the needle. This operation is faster but poses excessive strength requirements from the needle. In many cases, the logic behind high speed insertion is to reduce the pain associated with needle insertion and it is based on the fact that if the insertion is fast enough, the nerve system will not be as fast to respond. This is true only if the needle does not strike directly a big enough nerve sensor, e.g., pacinian corpuscle. Spring activation cannot control the depth of penetration and only a full penetration performed by the spring system activation can be achieved. Usually spring activation piercing apparatus is responsible only for the insertion or the retraction while the complement operation is done manually.

The present invention is teaching integration of the fabrication of a needle with the fabrication of a mechanical subsystem, which is responsible for the insertion and the retraction of the needle into and from the target object. The needle and the actuator are integrated into a single die or multi die structure using semiconductor fabrication techniques. Both the needle and the mechanical subsystem are fabricated using semiconductor fabrication techniques allowing achieving, among other things, very thin needles. Needles much thinner than stainless-steel needles can be achieved. Another advantage is the ability to manufacture, with a low cost, array of needles that in many applications has an advantage over a single piercing apparatus. The medical applications that will be made possible using such arrangement are described hereinafter. Having semiconductor micro mechanical (MEMS) system capability enables very flexible and accurate mechanical operation. For example, the needle may penetrate the object using very small movement steps, with a step resolution of several micro-meters. The penetration speed and force can be preciously controlled over time using digital micro controller that is optionally integrated into the needle system, optionally, on the same die. The ability of very slow insertion of the needle enables novel, not currently in use, scheme to avoid pain during treatment. When a needle is inserted very slowly, the pressure that the nerve system feels is lower than the pain threshold hence the patient does not feel the needle insertion. In addition, such scheme, that is not possible in current needle system technologies, enables reduction in the requirement for strength of the needle and enable thinner and more reliable needle system. Furthermore, the ability to stop the penetration in any depth, potentially with the aid of other monitoring signals in the loop, open the doors for many new feature such as (1) penetration to the exact depth in a tissue, e.g., the epidermis, the dermis, or the hypodermis; (2) avoid sticking a blood vassal; (3) targeting to a blood vassal; (4) avoid or targeting nerve sensors; (4) avoid or targeting hair papillae; (5) avoid or targeting sweat glades; and avoid or targeting lesions warts and moles.

As used herein, the term "die" means a rectangle chip fractured from a semiconductor wafer and manufactured in semiconductor foundry by semiconductor fabrication processes. The term "chip" and the term "die" are alternately used in this application and essentially mean the same. Note that the die is not necessarily made of semiconductor material rather is manufactured using facilities that are usually used to fabricate semiconductors dies.

As used herein, the term "substrate" means the material layer the wafer is made of which all additional layers and structures are fabricated on top of it. Each die or chip comprises a substrate which all other elements of the die or the chip are constructed on top of the substrate. Optionally, whenever the substrate is etched, elements of the die or the chip are constructed inside the substrate.

As used herein, the term "die plane" or the term "substrate plane" means the plane of the surface of the substrate that is used to fabricate the layers on top of it or any plane parallel to this plane if appropriate in the context of the sentence. The terms "die plane" and "substrate plane" are essentially the same and are used herein interchangeably.

The term "in plane" or "in-plane" relates to movement or any other operation in a plane that is parallel to the die plane, and the term "out-of-plane" means movement or any other operation in a plane that is not parallel to the die plane.

Optionally, the needle system or the piercing apparatus comprises an array of needles which enables activation of some of the needles in this array selectively based on the needle location.

Before explaining at least one embodiment of the invention in detail, it is to be understood that the invention is not necessarily limited in its application to the details of construction, fabrication techniques and the arrangement of the components and/or methods set forth in the following description and/or illustrated in the drawings and/or the Examples. The invention is capable of other embodiments or of being practiced or carried out in various ways.

Figure 1B:
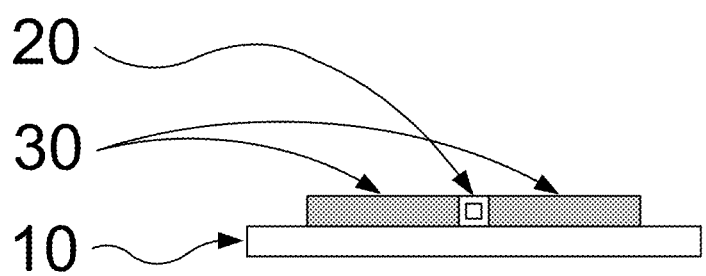
Figure 1C:
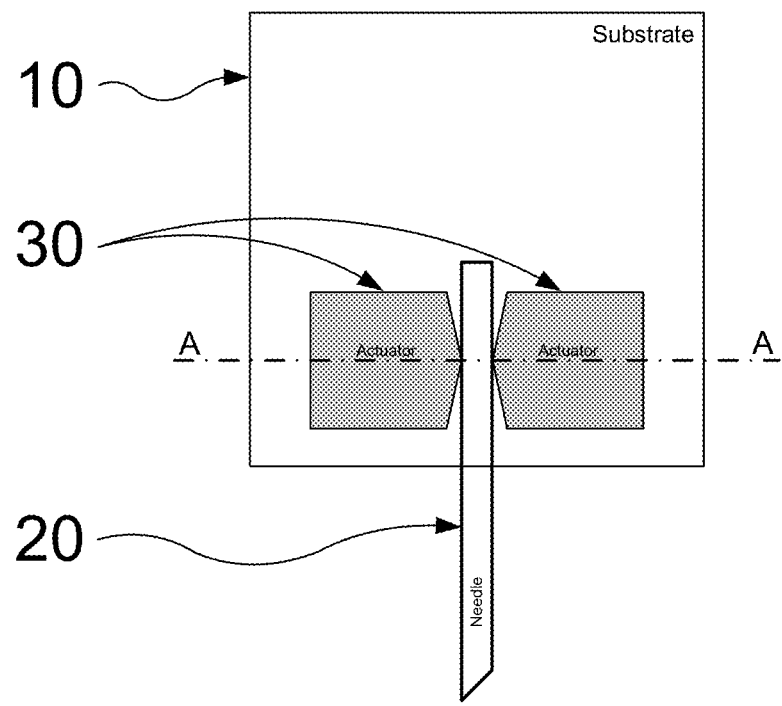

For purposes of better understanding some embodiments of the present invention, as illustrated in FIGS. 1-15 of the drawings, reference is first made to FIG. 1. FIGS. 1A-1C illustrate a principle simplified construction and operation of the present invention. FIG. 1A presents a top view of the piercing/needle apparatus in close, i.e., initial fabricated position. FIG. 1B presents a cross-sectional view of the needle apparatus across line A-A indicated in FIG. 1A. FIG. 1C presents the top view of the needle apparatus in fully open position. The simplified needle apparatus comprises a die substrate 10, a needle 20 and actuators 30. Needle 20 may be fabricated as a floating element over substrate 10 so it can be moved or slide over substrate 10. Needle 20 is attached to actuator 30 that moves or slides the needle relative to the die substrate 10. In specific, needle 20 can exceed die substrate 10 edges and get out of the die boundary in order to penetrate or pierce a target object if the object is attached or come in to proximity with the die edge. Needle 20 may be fabricated using silicon, silicon oxide, or any other materials that can be grown or printed on die substrate 10 using semiconductor fabrication processes. To achieve a floating needle structure the needle may be fabricated on top of a thin temporary layer (for example silicon oxide) that is etched away after needle fabrication. Optionally, to reduce the friction between die substrate 10 and needle 20, an array of small dimples is imprinted. Alternatively, needle 20 is held at all times on the air by actuators 30. needle 20 and actuators 30 are build such that a full accurate control of needle insertion is possible.

Needle 20 may be configured to move in plane with the die substrate 10 plane as shown in FIG. 1 or out of the die substrate plane 10 as demonstrated in FIGS. 5 and 9.

Both the depth of insertion and the velocity of insertion may be adjustable. It is also possible to retract the needle back to its initial position inside substrate 10. Retraction time and retraction velocity may also be fully controlled.

A single die may comprise a plurality of actuators and a plurality of needles with any one of or any combination of one to one, one to many and many to one actuators to needles relationships.

As used herein, the term "actuator" means an element or a component or a circuit or a complex of elements that are configured to mechanically move or displace another element, e.g., a needle.

As used herein, the term "needle" means an elongated element that is configured to mechanically pierce or penetrate an object. The tip of the needle may be sharp to ease the penetration to the object. The strength, length and width of the needle may varies depend on the pierced object and the purpose of the use. The needle may be hollow in order to inject or suck materials through the needle. Needle may have additional elements such as conductive or resistive elements over the elongated body or in the tip area.

Figure 2:
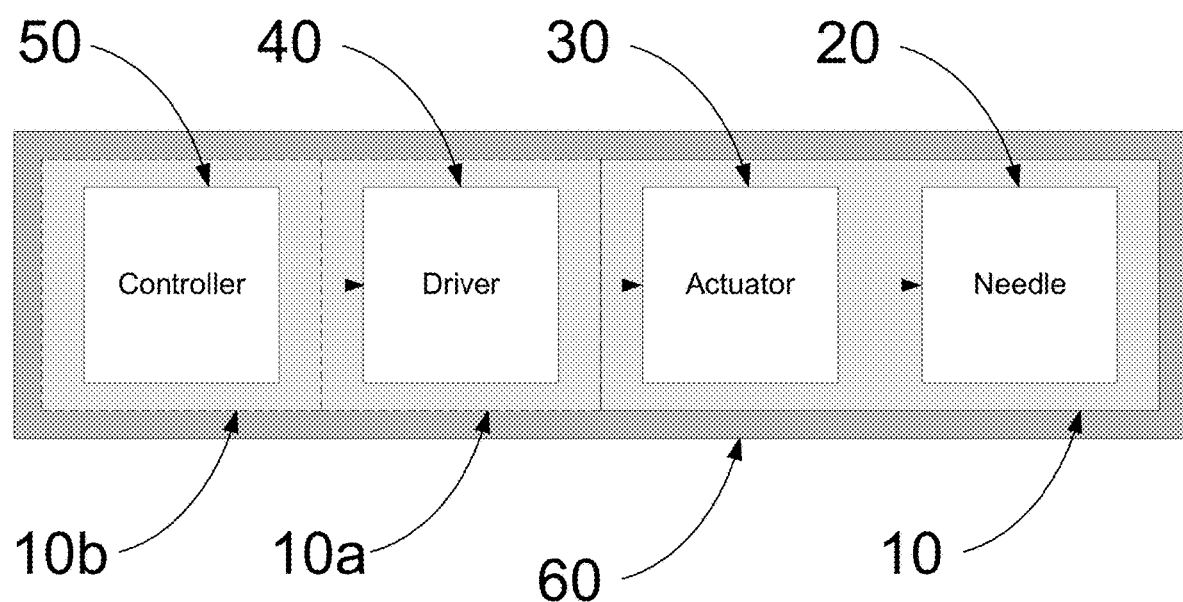
FIG. 2 is a block diagram of a minimal simplified piercing apparatus in accordance with the present invention.
Figure 3:
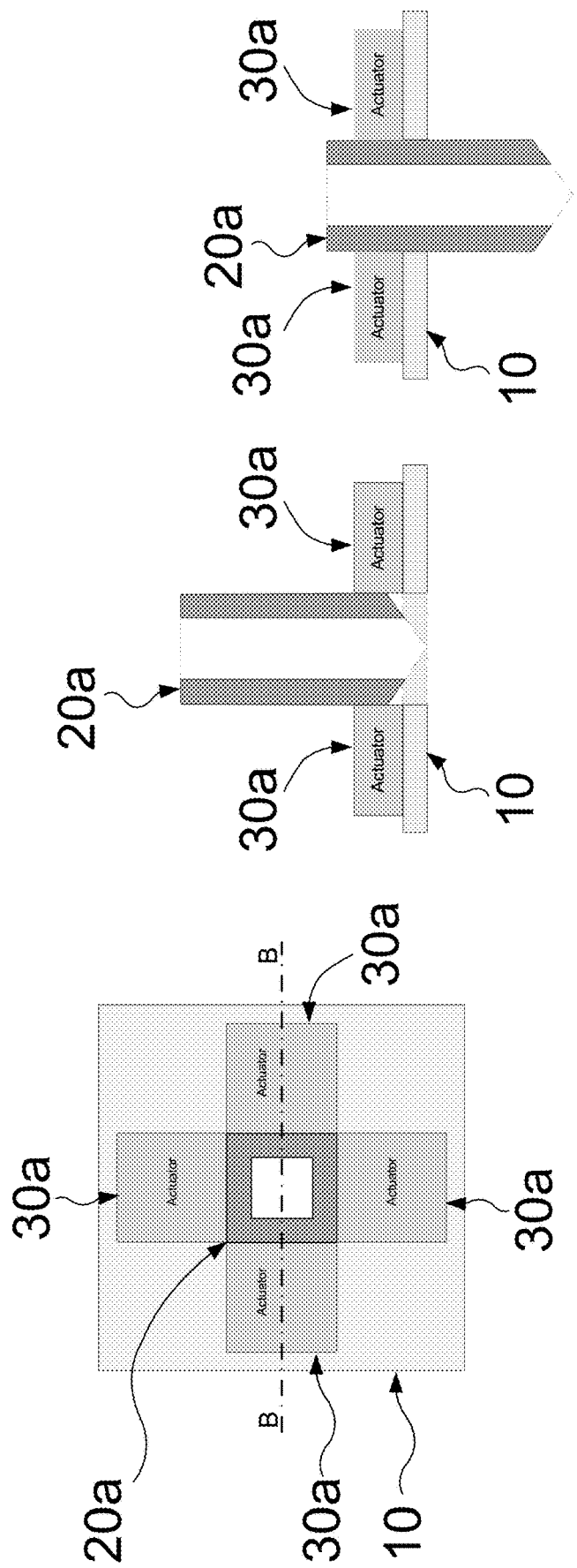
FIG. 3A-FIG. 3C are illustration of construction and operation of out-of-plane needle implementation according to the present invention.

Reference is now made to FIG. 2. FIG. 2 illustrates a block diagram of a minimal simplified piercing apparatus in accordance with the present invention. Needle 20 is a needle as illustrated in FIG. 1. Actuator 30 is in contact with Needle 20 and can move needle 20 between initial position and fully open position, as illustrated in FIG. 1. Actuator 30 moves needle 20 according to signal from an actuator driver 40. Actuator driver 40 drives current or voltage signals to activate actuator 30. Optionally, driver 40 drives multiple signals to activate actuator 30. Optionally, driver 40 drives complex signaling like sine waves, pulse waves or any complex time function signals to activate actuator 30. Optionally, driver 40 drives digital signaling to activate actuator 30. Typically, driver 40 is implemented using analog electronic elements such as transistors. As used herein, the term "actuator driver" means an element or a component or a circuit or a complex of elements that are configured to electrically signaling and controlling the actuator operation.

Piercing apparatus comprising a controller and one or more dies as illustrated in FIG. 1. The piercing apparatus is controlled by the controller 50. Controller 50 instructs the driver to generate the appropriate signals to move needle 20. Controller 50 determines system level operation parameters, such as, when will the insertion of the needle starts?, how much time and in what velocity the needle will penetrate?, what will be the depth of penetration?, how much time the needle will be inside the object?, how much time it will take to retract the needle?, etc. Typically, controller 50 is implemented as a digital micro controller with a processor, memories and peripherals. Typically, the controller runs embedded software from its local memory.

Needle 20 and actuator 30 are fabricated on a single semiconductor die 10 as illustrated in FIG. 1. Driver 40 is optionally fabricated on the same die, i.e., die 10, or alternatively on independent die, die 10a. Controller 50 is optionally fabricated on the same die, i.e., die 10, or alternatively on independent die, die 10b. When needle 20, actuator 30, driver 40 and controller 50 are integrated on the same die, a complete piercing apparatus in a single die is implemented. Optionally, die 10a and die 10b are implemented as a single die and the full piercing apparatus is implemented as a two die solution. In an exemplary embodiment of the invention, die 10a and die 10b are attached back to back with die 10 using wafer bonding techniques and the connection between the dies is using vias through each wafer. Such a configuration has several advantages. Optionally, piercing apparatus has external package 60. External package 60 size and shape depends on the actual application of the piercing apparatus and the object or organ it is aimed to penetrate to. For example, an adhesive patch package may be used to attach the piercing apparatus to a skin portion. In a different application the package may contains straps to tight the piercing apparatus to the organ. To fulfill sterilization requirements external package 60 may be sealed with a dedicated pierce-able membrane to enable needles to get out from package 60.

Reference is now made to FIGS. 3A-3C. FIG. 3A-3C illustrate a principle simplified construction and operation of out-of-plane (the die or substrate plane) needle implementation according to the present invention. In FIG. 3A a top view of the die is illustrated. In FIG. 3B a cross-sectional view of the die view across line B-B indicated in FIG. 3A when the needle is in initial close state. In FIG. 3C a cross-sectional view of the die when the needle is in open penetrated state. Reference is now made to FIG. 3A. A square needle 20a with internal hollow cavity is fabricated with four actuators 30a holding needle 20a from all four sides. The actuator and the needle are fabricated on top of a substrate 10. Reference is made now to FIG. 3B. FIG. 3B is a cross-sectional view over line B-B drawn in FIG. 3A. In this figure, the via in substrate 10 is presented. Only two actuators 30a are visible in cross section and needle 20A is perpendicular to substrate 10 plane. The needle is in the position where it is fabricated, i.e., in initial/close state. Reference is made now to FIG. 3C.

FIG. 3C is the same cross-sectional view over line B-B drawn in FIG. 3A. Needle 20a in this figure is in its open penetrated state. Needle 20a traveled through the via in substrate 10 and is crossing substrate 10 bottom plane. In case there is a skin tissue attached to the die, the needle in this state would be penetrating the skin.

Many types of MEMS actuators can be used to move or drive the needle. The most common options are electrostatic, electro-magnetic, thermal and piezoelectric. Piezoelectric actuation is a good choice due to its relative high force concentration and low power consumption. An in-plane type embodiment of piezoelectric actuation is illustrated in FIG. 4.

Figure 4:
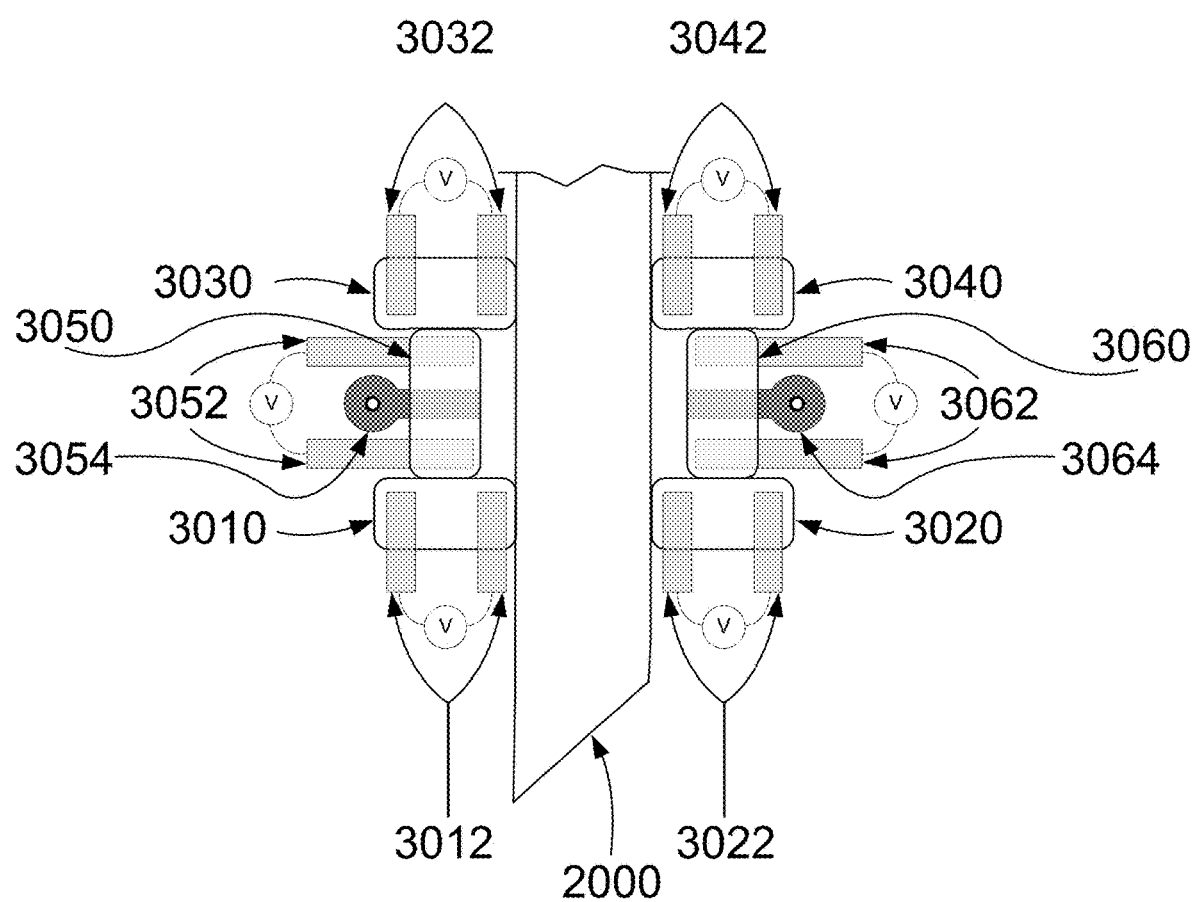
FIG. 4 is a top view of needle actuation and locking subsystem using piezoelectric actuators in accordance with a preferred embodiment of the invention.

Reference is now made to FIG. 4. FIG. 4 illustrates an example of needle actuation and locking subsystem using piezoelectric actuators. The figure is a top view of the fabricated structure and for clarity only the relevant elements are shown. In rest position, needle 2000 is locked or griped by four piezoelectric crystals 3010, 3020, 3030 and 3040. Each piezoelectric crystal 3010, 3020, 3030 and 3040 have a pair of electrodes 3012, 3022, 3032 and 3042 located on the crystal's edges. The applying voltage, induce an electric field in the same direction as the polarity of the piezoelectric crystal. Applying a positive voltage to electrodes 3012, 3022, 3032 and 3042 expand the crystals, hence increase the gripping force on needle 2000, and tighten the locking of needle 2000 to its position. Applying negative voltage to electrodes 3012, 3022, 3032 and 3042 contract the crystals, hence free the needle to move. The full step motor structure contains additional two piezoelectric crystals 3050, 3060, each one of them is located on the opposite side relative to needle 2000. Electrodes 3052 are connected to piezoelectric crystal 3050 and electrodes 3062 are connected to piezoelectric crystal 3060. Piezoelectric crystal 3050 is mechanically attached to the die using anchor 3054. Piezoelectric crystal 3060 is mechanically attached to the die using anchor 3064. During needle insertion motion, i.e., motion downwards in the figure, the needle system controller initiates a specific sequence of instructions as described herein. In the first step, crystals 3030 and 3040 expand and crystals 3010 and 3020 contract so that the needle is hold only by crystals 3030 and 3040. Next, crystals 3050 and 3060 contract and since crystals 3050 and 3060 are anchored to the die, needle 2000 move downwards. Next, crystals 3010 and 3020 contract and hold needle 2000. Next, crystals 3030 and 3040 contract, therefore they release their grip from needle 2000. The next step is expanding of crystals 3050 and 3060 that cause needle 2000 to further move downwards. This cycle can continue as long as the controller requires to insert needle 2000 further into the target organ or object. To retract needle 2000, a similar sequence is applied, but now, the controller contracts crystals 3050 and 3060 when crystals 3010 and 3020 hold needle 2000, and expands crystals 3050 and 3060 when crystals 3030 and 3040 hold needle 2000. Other structures of piezoelectric configuration with different structure of crystals and electrodes may be used as well. This mechanism can also be used as an ultrasound transducer, i.e., ultrasound transmitter and receiver, to capture an image of the object using the needles. In order for the needle to acts as an ultrasonic transmitter, the needle is gripped by crystals 3010 and 3020 or by crystals 3030 and 3040 and crystals 3050 and 3060 electrodes are fed by electrical signals that vibrate the needle in ultrasonic frequencies; Similarly, for the needle to act as an ultrasonic receiver, the needle vibrates by the received ultrasonic wave and crystals 3050 and 3060 are contracted or expanded by the impinging ultrasonic wave and create an electronic signal. The signals created by crystals 3050 and 3060 electrodes 3052 and 3062 are amplified and feed a monitoring subsystem. Conditioned upon the transmitted and received ultrasound signals, the monitoring subsystem generates an image of the object that the needles are in contact therewith. Needle vibration can act also as a stimulus and as a source of heating.

Out of die Implementation

In previous exemplary embodiment, an in-plane embodiment where the needle slides on the die plane is presented. In in-plane embodiments a single die may comprise a 1D array of needles. A single die implementation capable of incorporating a 2D array of needles is possible when the needles move out of plane (e.g., perpendicular to the die plane). Such an exemplary embodiment is presented in FIG. 5.

Figure 5A:
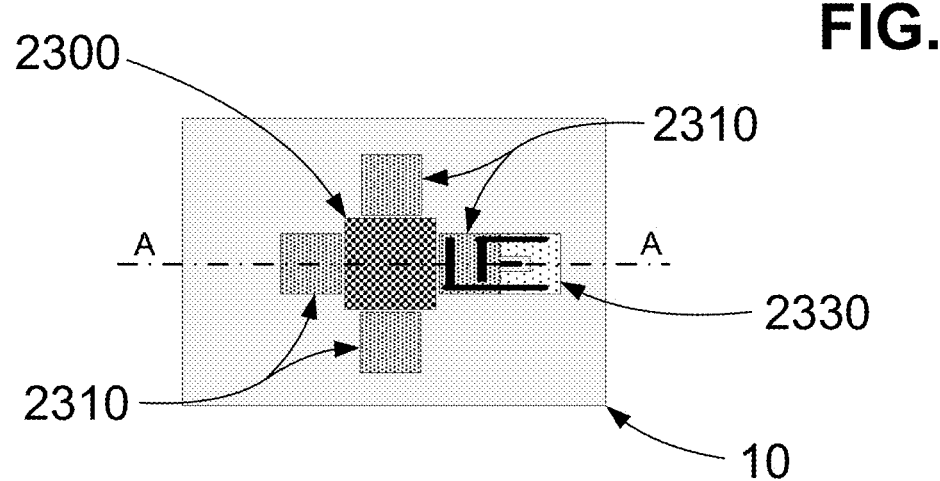
FIG. 5A-FIG. 5B are illustrations of out of die plane moveable needle embodiment in accordance with the present invention.
Figure 5B:
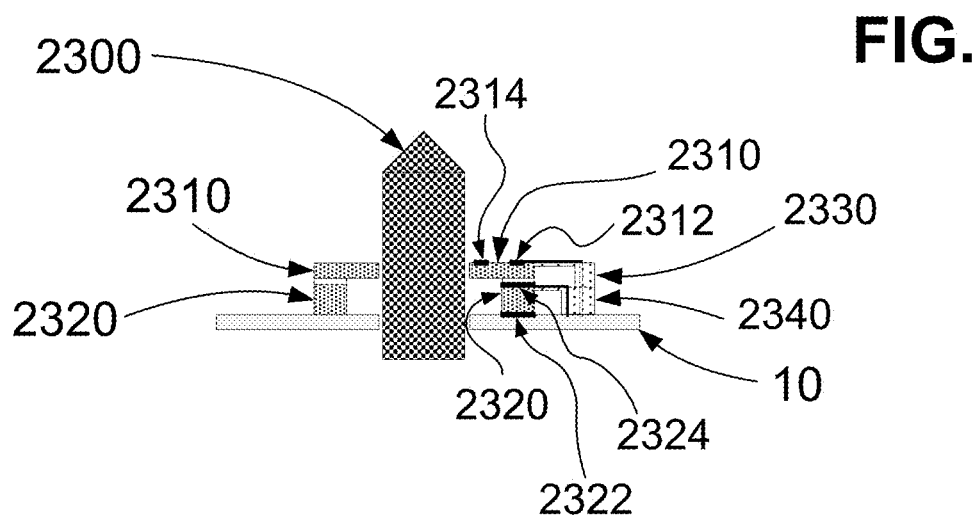

Reference is now made to FIG. 5. FIG. 5 illustrates exemplary embodiment of single out-of-die-plane or out of substrate 10 plane movable needle. Typically, the die will have an array with plurality of such needles. FIG. 5A is a top view of the die, and FIG. 5B is a cross section side view across line A-A of FIG. 5A. Needle 2300 is gripped by four piezoelectric crystals 2310 one from each side of needle 2300. The grip of each side of needle 2300 can be held or released by expand or contract each crystal 2310. Each piezoelectric crystal 2310 lays over another piezoelectric crystal 2320 (seen only from the side view in FIG. 5B) with an electric isolation layer between the two crystal pair 2310, 2320. Four pairs of piezoelectric crystals 2310, 2320 surround needle 2300. When the piezoelectric crystals 2320 extract while crystals 2310 hold needle 2300, the needle is lifting up. When the piezoelectric crystals 2320 contract while crystals 2310 hold needle 2300, the needle is retracting back.

Each piezoelectric crystal 2310 has two electrodes, 2312 and 2314, located on the crystal's edges (for sake of clarity only the electrodes of the right-side crystal have been illustrated in FIG. 5). Each piezoelectric crystal 2320 has two electrodes, 2322 and 2324, located on the crystal's edges (for sake of clarity only the electrodes of the right-side crystal have been illustrated in FIG. 5). In order to electrically connect electrodes 2312, 2314, 2322 and 2324 to substrate 10, cantilevers structure is fabricated over substrate 10. The cantilever structure comprises bottom cantilever 2340 and top cantilever 2330 lays over bottom cantilever 2340. For the sake of clarity only the right-side cantilevers structure has been illustrated in FIG. 5. In reality, a cantilevers structure 2330, 2340 is located beside each crystal pair 2310, 2320. The bottom electrode 2322 is laying on surface of substrate 10, hence electrode 2322 is connected easily to conducting traces on substrate 10. Electrode 2324 is connected to substrate 10 through beam 2340. The connection is done by conductive via inside beam 2340, via inside top cantilever 2330 and conductive trace over beam 2340. Beam 2340 is designed to be flexible enough to support crystal 2320 expand or contract. Electrode 2312 is connected to substrate 10 through beam 2330. The connection is done by conductive via inside the anchors of beam 2340 and 2330 and conductive trace over beam 2330. Electrode 2314 is connected to substrate 10 through beam 2330 as well. The connection is done by conductive via inside the anchors of beams 2340 and 2330 and conductive trace over beam 2330. The traces on beam 2330 are imprinted in parallel on both sides of the beam, as illustrated by the top view in FIG. 5A. Beam 2330 is designed to be flexible enough to support the movement of crystal 2310 caused by the expansion or the contraction of crystal 2320.

Needle 2300 insertion or retraction motion, i.e., motion upwards or downwards respectively in FIG. 5B, is performed by a specific sequence of crystals expansion and contraction in similar manner to the one describes in companion to FIG. 4 hereinabove. The sequence is done using opposite pairs of crystals 2310, one pair grips the needle and the other pair releases the needle to perform a movement that does not affect the needle movement. The pairs are alternating their role between grip and release. During needle lock all four crystals 2310 expand to grip needle 2300 tightly. It is appreciated that other variation of in-plane and out-of-plane embodiments of needle movement are possible. Other needle style, actuator types and structures as well as support subsystem such as driving and connecting the various elements are all falling into the scope of the invention.

Piezoelectric Stack Implementation

In the embodiments of FIG. 4 and FIG. 5 each actuator is using single bulk piezoelectric crystal which has a relatively small displacement or alternatively need a large operating voltage to provide a sufficient displacement. To overcome this limitation a stack version of piezoelectric actuator may be used.

Figure 6:
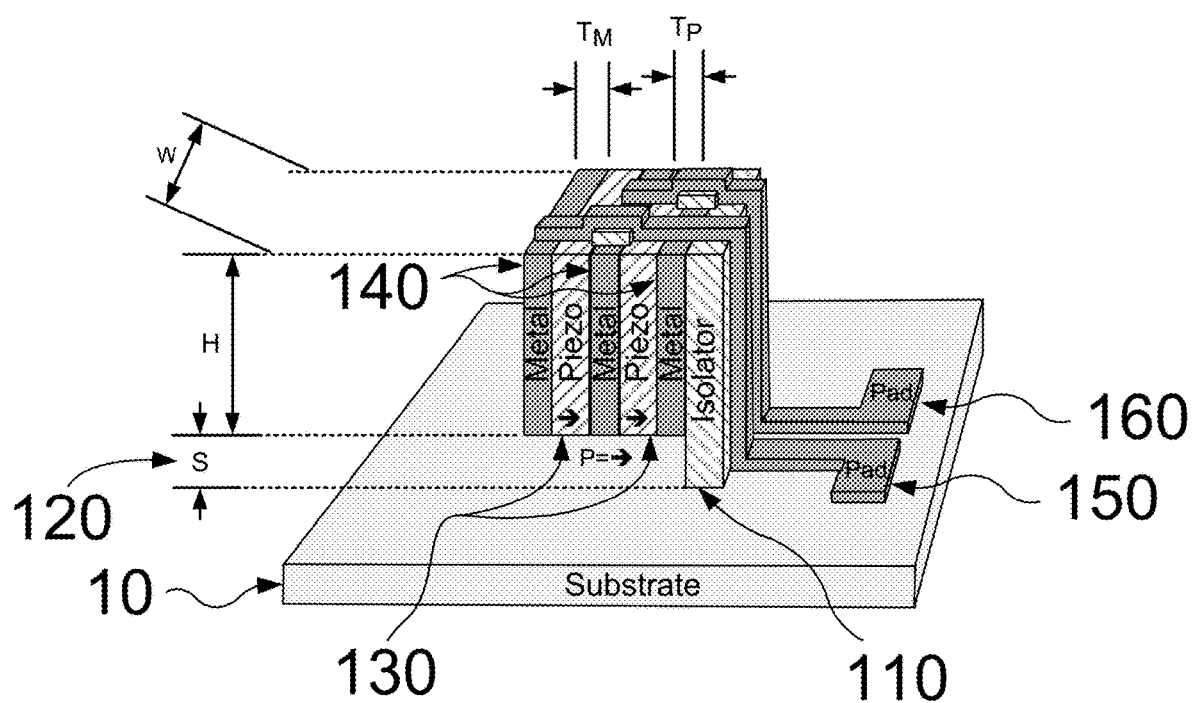
FIG. 6 is an isometric view of a piezoelectric stack actuator in accordance with the present invention.

Reference is now made to FIG. 6. FIG. 6 illustrates a 3D isometric view of a stack version of a single piezoelectric actuator. Substrate 10 is connected to an anchor 110 made of isolation material. Adjacent to the anchor isolator 110 (to the left of the isolator in the figure) a stack of tiles of piezoelectric materials 130 interleaved with tiles of metal electrodes 140 are fabricated joined to each other over a sacrificial layer 120 with thickness S. Sacrificial layer 120 is not shown in the figure since it is etched away at the final stage of fabrication. Instead, an air gap is shown in the figure. The piezoelectric tiles 130 have height H and wide W. The thickness of metal electrodes tiles 140 is $T_M$ and the thickness of the piezoelectric material tiles 130 is Tp. Typically, H and W can range between 10 micro-meters to 100 micro-meters. Additionally or alternatively, H and W range may be from 1 micro-meter to few millimeters. The thickness of electrodes 140 may be as thin as 100 angstroms and the thickness of the piezoelectric tile 130 may get down to few microns. In the figure, for the sake of clarity, only two piezoelectric tiles and three electrodes are shown, but in reality tens or even hundreds of piezoelectric tiles may be fabricated for a single actuator. The driving voltage that is provided to the stack actuator is the same for each second electrode. The odd electrodes are connected to a first pad 150 and the even electrodes are connected to the second pad 160. To maximize the displacement to the left direction, the polarity of the piezoelectric is configured to be parallel to the axis of displacement as illustrated in the arrows inside the tile and adjacent to the polarization symbol P.

Figure 7A:
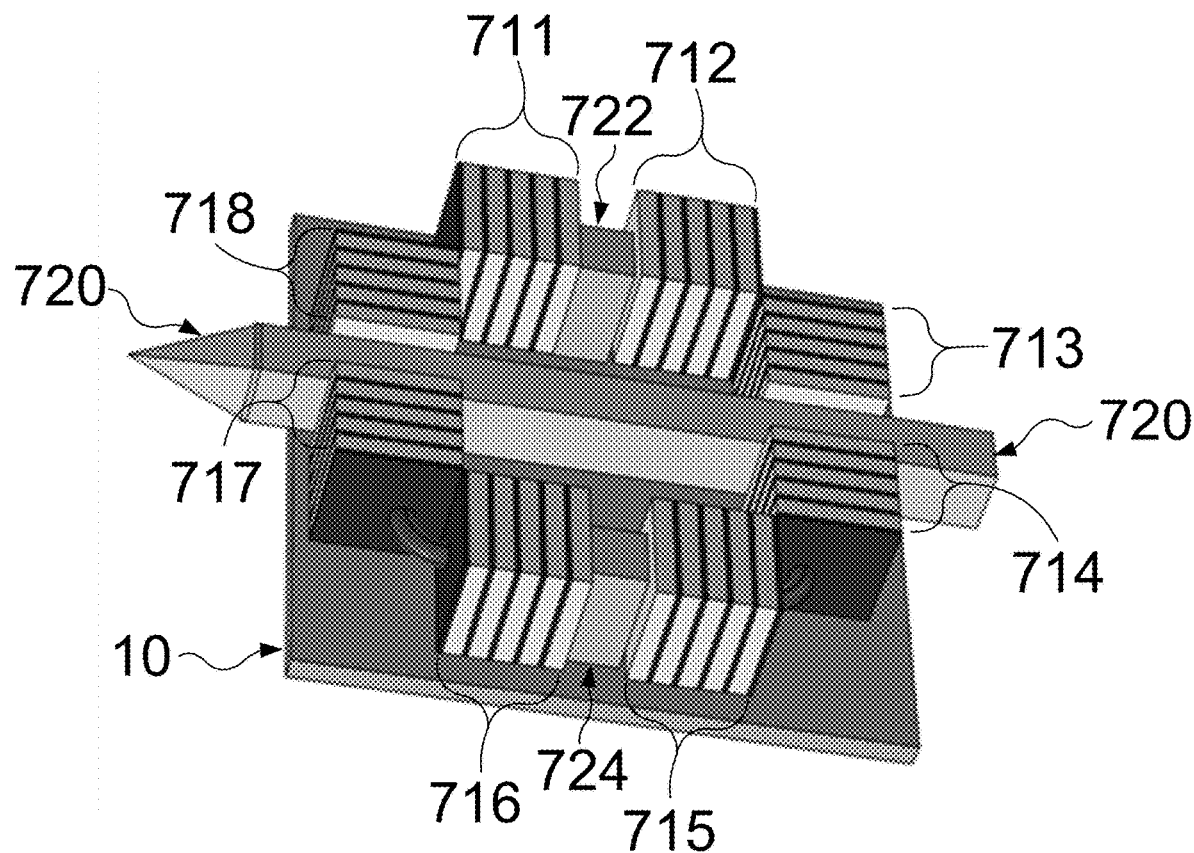
FIG. 7A-FIG. 7B are illustrations of a step motor comprises piezoelectric stack actuators in accordance with the present invention.

Reference is now made to FIG. 7A. FIG. 7A is isometric view of a needle step motor embodiment similar to the one illustrated in FIG. 4 but with piezoelectric stack actuator that was presented in FIG. 6. Eight piezoelectric stack actuators 711, 712, 713, 714, 715, 716, 717 and 718 are fabricated in this exemplary embodiment. Piezoelectric stack actuators 711-718 in this illustration are with five piezoelectric tiles each. Piezoelectric stack actuators 713, 714, 717 and 718 grip a needle 720. Between piezoelectric stack actuators 711 and 712 there is an anchor 722 that connects the actuator structure to a substrate 10. Between piezoelectric stack actuators 715 and 716 there is an anchor 724 that connects the actuator structure to a substrate 10. Piezoelectric stack actuators pairs (711, 718), (712, 713), (714, 715) and (716, 717) are connected to each other. In the figure the connection is realized by a quarter of a ring for the sake of clear visualization. The actual mechanical connection between these actuators pairs may vary between different embodiments.

Figure 7B:
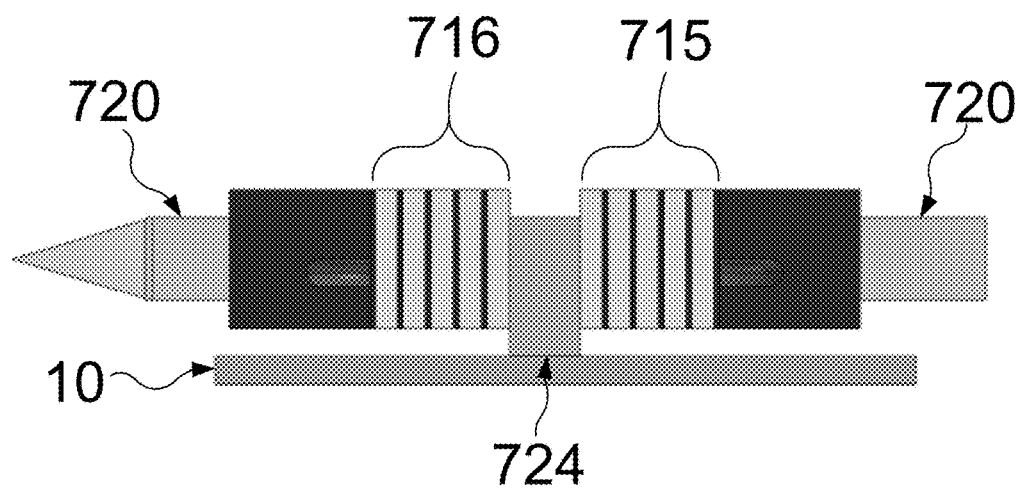

Reference is now made to FIG. 7B. FIG. 7B is a side view of the step motor embodiment illustrated in FIG. 7A. In this side view, one can see better the air gap between the substrate and the piezoelectric stack actuators. This gap is created by etching away sacrificial layer or etching away part of the substrate as will be discussed later on.

Figure 8A:
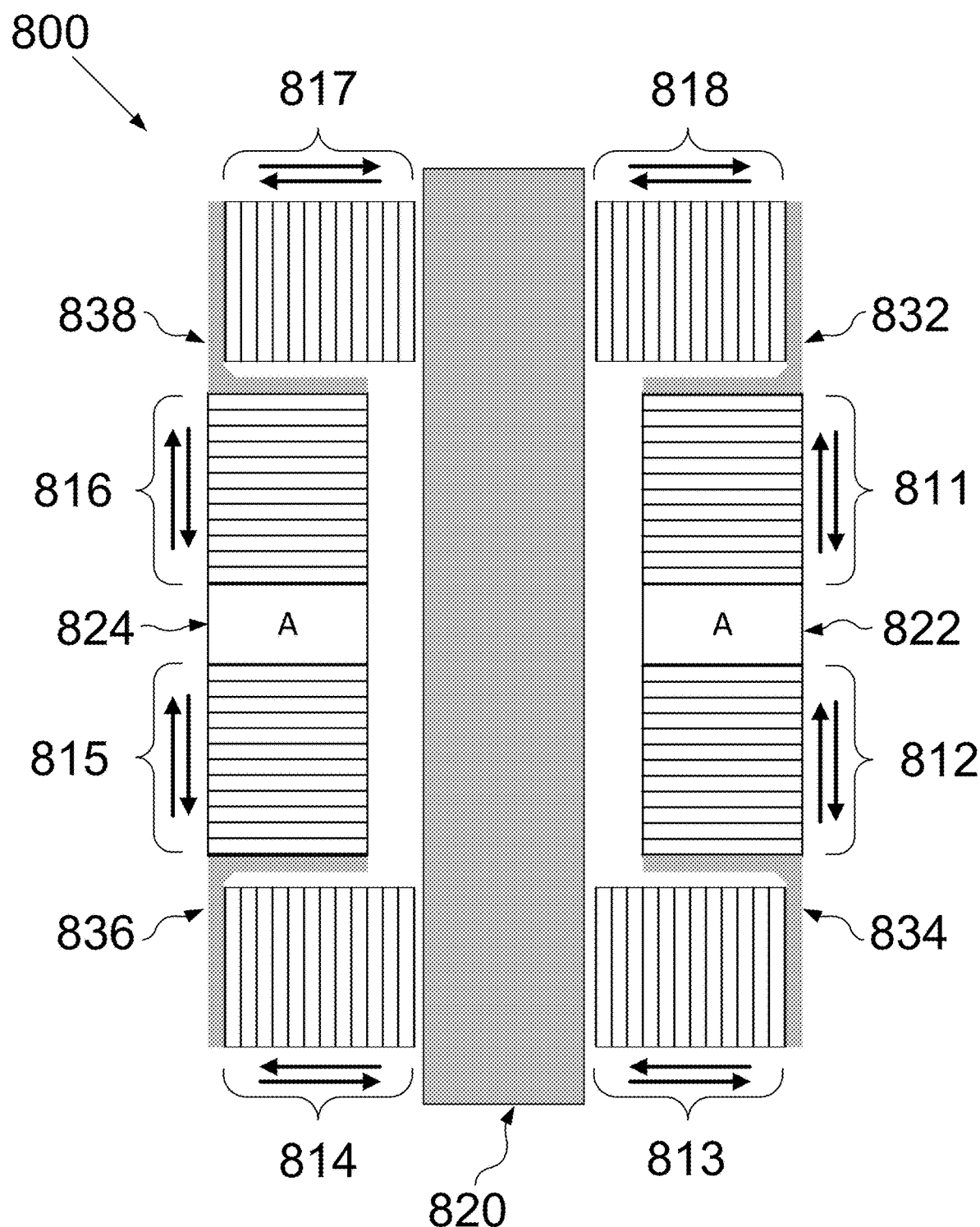
FIG. 8A-FIG. 8B are illustrations of another step motor comprises piezoelectric stack actuators in accordance with the present invention.

Reference is now made to FIG. 8A. FIG. 8A illustrates a zoom-in top view of a step motor 800 with piezoelectric stack actuator embodiment similar to the one presented in FIGS. 7A and 7B. The actuators 811, 812, 813, 814, 815, 816, 817 and 818 are piezoelectric stack actuators with twelve piezoelectric tiles each. The movement direction of each of piezoelectric stack actuator 811-818 is illustrated by the arrows adjacent to each one of the actuators. Part of a Needle 820 is illustrated in the figure. The anchors 822 and 824 holding actuator 811, 812, 815 and 816 above the substrate (not shown in the figure). Piezoelectric stack actuators 818, 813, 815 and 817 are connected to piezoelectric stack actuators 811, 812, 814 and 816 via L-shape joints 832, 834, 836 and 838 respectively.

When piezoelectric stack actuators 813, 814, 817 and 818 expand they grip needle 820. When piezoelectric stack actuators 813, 814, 817 and 818 contract they release needle 820. Piezoelectric stack actuators 811, 812, 815 and 816 create the movement of the needle (downwards or upwards in the figure). In initial state piezoelectric stack actuators 813, 814, 817 and 818 are expanded and hold needle 820 in lock position. The sequence of moving the needle downwards is as follows:

(1) contract piezoelectric stack actuators 813 and 814→lower grip is released;
(2) contract piezoelectric stack actuators 811 and 816→piezoelectric stack actuators 817 and 818 grip needle 820 and push needle 820 downwards due to contraction of piezoelectric stack actuators 811 and 816 that is fixed to the substrate via the anchors 822 and 824;
(3) expand piezoelectric stack actuators 813 and 814→holds back the needle with the lower grip;
(4) contract piezoelectric stack actuators 817 and 818→upper grip is released;
(5) expand piezoelectric stack actuators 812 and 815 and expand piezoelectric stack actuators 811 and 816→lower grip hold needle 820 and push needle 820 downwards due to expand of piezoelectric stack actuators 811 and 816 movement relative to anchors 822 and 824. Piezoelectric stack actuators 811 and 816 are getting ready for their next needle movement step;
(6) expand piezoelectric stack actuators 817 and 818→holds back the needle with the higher grip;
(7) Go back to step (1). This sequence can continue until the needle is inserted to the desired depth.

The upward movement of the needle is done in a similar way only when the lower grip (piezoelectric stack actuators 813 and 814) holds the needle piezoelectric stack actuators 812 and 815 contract, and when the higher grip (piezoelectric stack actuators 817 and 818) holds needle 820 piezoelectric stack actuators 811 and 816 expand.

Vibrating needle 820 is achieved by holding needle 820 with piezoelectric stack actuators 817 and 818 and providing AC signal to piezoelectric stack actuators 811 and 816 or by holding the needle with piezoelectric stack actuators 813 and 814 and providing AC signal to piezoelectric stack actuators 812 and 815. Sensing vibration can be performed by holding the needle with piezoelectric stack actuators 817 and 818 and reading the voltage developed on piezoelectric stack actuators 811 and 816 or similarly, by holding the needle with piezoelectric stack actuators 813 and 814 and reading the voltage developed on piezoelectric stack actuators 812 and 815

An acoustic wave that will propagate through the needle can be generated by holding the needle with both piezoelectric stack actuators 817 and 818 and piezoelectric stack actuators 813 and 814 and vibrating piezoelectric stack actuators 811 and 816 or piezoelectric stack actuators 812 and 815. vibrating piezoelectric stack actuators 811 and 816 and piezoelectric stack actuators 812 and 815 simultaneously with opposite phase may be used to create twice as stronger acoustic wave.

Figure 8B:
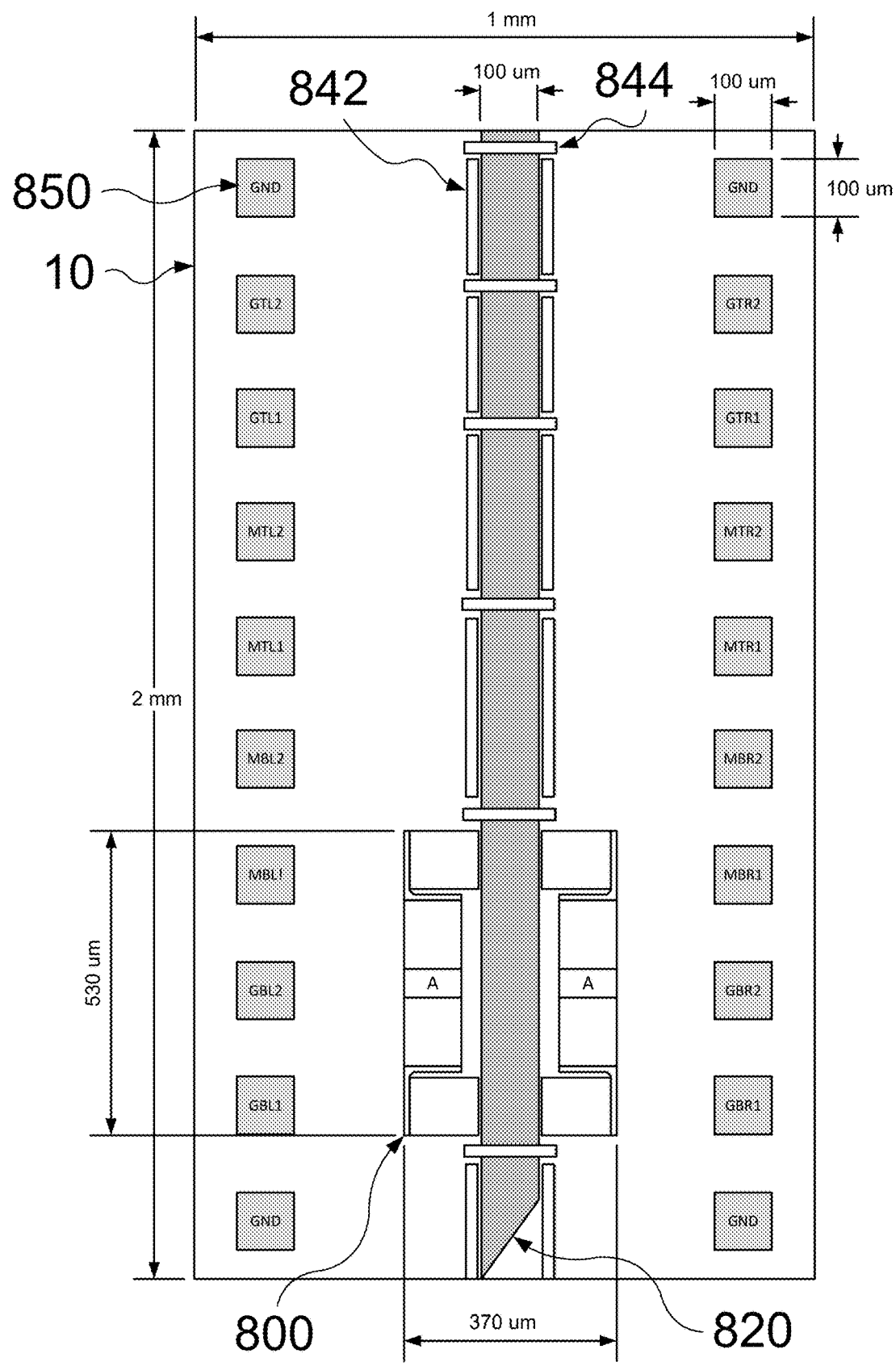

Reference is now made to FIG. 8B. FIG. 8B illustrates a top view of the full die comprising piezoelectric step motor 800 and a needle 820 according to an exemplary embodiment of the invention. The substrate 10 size or the die size, in this exemplary embodiment, is 2×1 mm. Needle 820 is 100 um wide and 2 mm length and located on the center of substrate 10. Step motor 800 with its eight piezoelectric stack actuators 811-818 is 370 um wide and 530 um long and located in the bottom part of substrate 10. To prevent undesired needle movement from its allowed position and to allow sliding only downwards and upwards, ten elongated side limiters 842 and six top bridge limiters 844 are deployed along needle 820 location. In addition, ten electric contact pads are deployed on each side of the substrate 10. Pads size is 100 um×100 um. The upper and lower pads on each side of the die are connected to substrate 10 and are used as electric ground reference. The other eight pads on each side of the die are connected to the four actuators on each side of the die. Each actuator is driven by electric signal applied to the two corresponding pads. For clarity of the illustration, the routing between the pads and the electrodes of the piezoelectric stack actuators are not shown. The routing is done by adding one or more metal layers, and optionally, one or more isolation layers. The pads may be connected to actuator drive 40 (shown in FIG. 2) that activate the actuators. In an exemplary embodiment of the invention, pads 850 are crossing substrate 10 to create conductive vias and are connected back to back to the die of drivers 40. Drivers 40 die is fabricated separately and bond to the actuators die using wafer bonding technics.

Out of Die Implementation

Similar to the concept of having piezoelectric stack actuators for the in (die) plane configuration it is also possible to have piezoelectric stack actuators instead of a bulk piezoelectric actuators in the out of (die) plane, i.e., perpendicular to the die plane configuration as demonstrated in FIGS. 9A-9D.

Figure 9A:
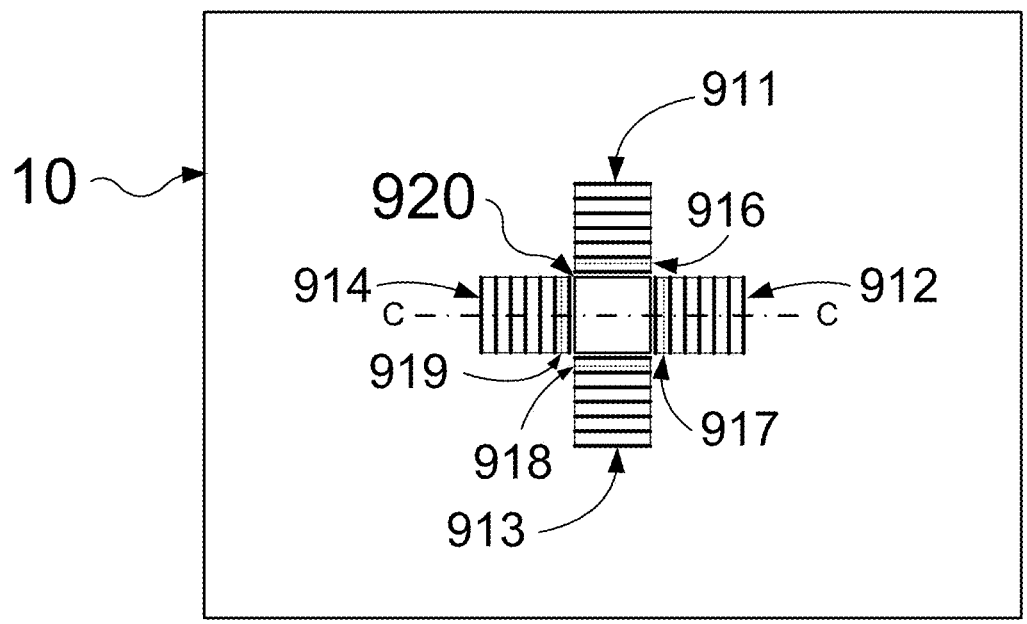
FIG. 9A-FIG. 9D are illustrations of an out-of-plane needle movement step motor comprising piezoelectric stack actuators in accordance with the present invention.

Reference is now made to FIG. 9A. FIG. 9A illustrates a top view of a step motor with piezoelectric stack actuator structured in out-of-plane needle movement configuration. Piezoelectric stack actuators 911, 912, 913 and 914 surround a square cross section needle 920 from all four needle 920 sides. Each piezoelectric stack actuator 911, 912, 913 and 914 comprises six piezoelectric tiles. Under each piezoelectric stack actuator 911, 912, 913 and 914, there is another piezoelectric stack actuator 916, 917, 918 and 919, respectively. Piezoelectric stack actuator 916, 917, 918 and 919 are hidden in this view and are represented by a dashed lines illustrate their end side that is close to needle 920. Piezoelectric stack actuator 916, 917, 918 and 919 are connected to substrate 10 as can be seen in FIG. 9B.

Figure 9B:
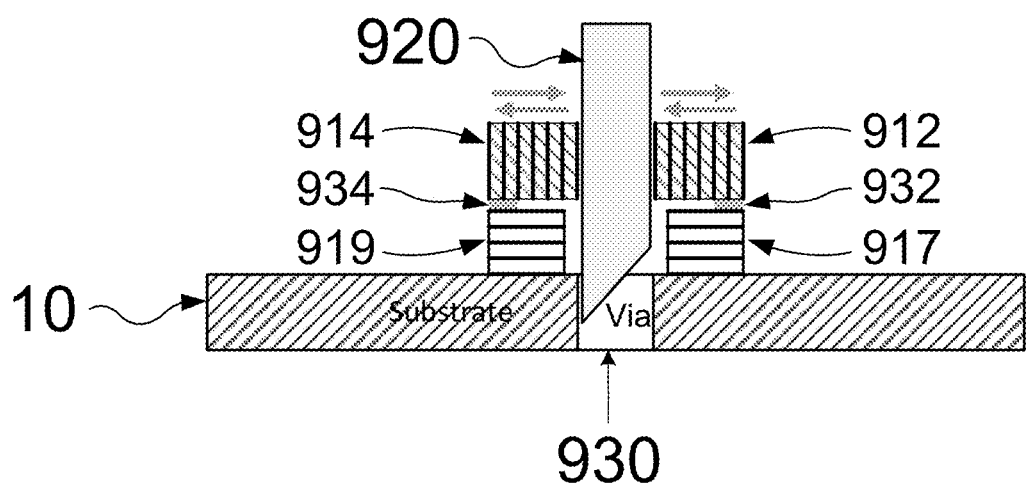

Reference is now made to FIG. 9B. FIG. 9B illustrates a cross section view of the step motor of FIG. 9A across line C-C. Substrate 10 comprises via 930 to allow needle 920 pass through substrate 10. Needle 920 may be gripped by piezoelectric stack actuators 912 and 914 by contract or expand as illustrated by the grey arrows above the actuators. Needle 920 may be gripped as well by contraction or expanding of piezoelectric stack actuators 911 and 913 (not shown in the figure). Piezoelectric stack actuators 917 and 919 are connected to substrate 10 and comprises four piezoelectric tiles each. Similarly, piezoelectric stack actuators 916 and 918 (not shown in the figure) are connected to the substrate 10 as well and comprises four piezoelectric tiles each. Piezoelectric tiles orientation of piezoelectric stack actuators 911, 912, 913 and 914 is perpendicular to substrate 10 plane while piezoelectric tiles orientation of piezoelectric stack actuators 916, 917, 918 and 919 is parallel to substrate 10 plane. The polarization of the piezoelectric tiles is opposite, i.e., tiles polarization of piezoelectric stack actuators 911, 912, 913 and 914 is parallel to substrate 10 plane, while tiles polarization of piezoelectric stack actuators 916, 917, 918 and 919 is perpendicular to substrate 10 plane. The connection between piezoelectric stack actuators 911, 912, 913 and 914 and piezoelectric stack actuators 916, 917, 918 and 919 is made by isolator layer 931 (not shown in the figure), isolator layer 932, isolator layer 933 (not shown in the figure) and isolator layer 934 respectively. To move the needle, piezoelectric stack actuators 911, 912, 913 and 914 hold and release needle 920 in pairs (911 and 913, 912 and 914) and the piezoelectric stack actuators 916, 917, 918 and 919 expand to move needle 920 upwards or contract to move needle 920 downwards. Needle 920 moves through via 930 in substrate 10 as illustrated in FIG. 3C. In an exemplary embodiment of the invention, needle 920 is fabricated independently and is assembled into the die.

As mentioned above, piezoelectric stack actuators 916, 917, 918 and 919 are fabricated by piezoelectric material layers that are parallel to substrate plane and piezoelectric stack actuators 916, 917, 918 and 919 are fabricated by piezoelectric material section (tiles) that are perpendicular to substrate plane. Parallel to substrate plane layers are easier to fabricate. Perpendicular to substrate plane tiles may be fabricated using lift-off process which is more complex. An out-of-plane design with only parallel to substrate 10 plane layers can be achieved by setting different polarization as described in FIG. 9C.

Figure 9C:
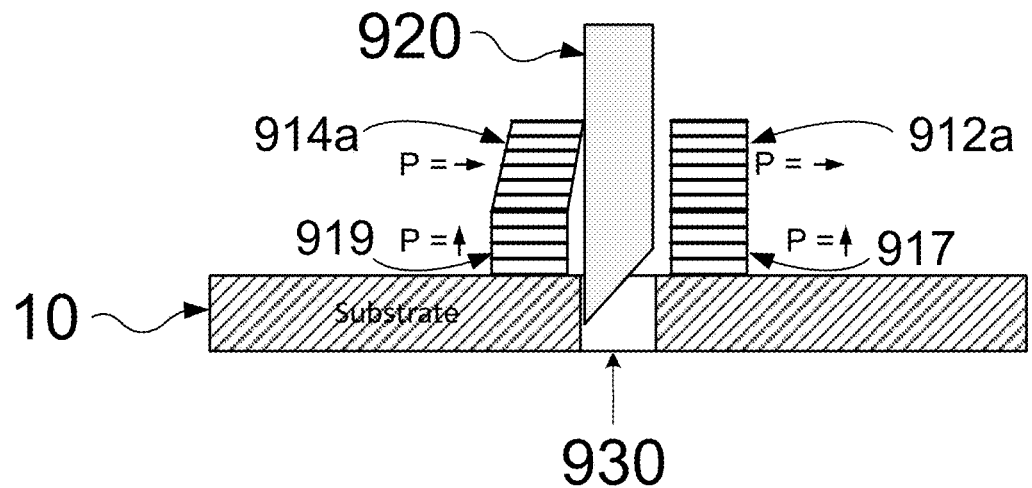

Reference is now made to FIG. 9C. FIG. 9C illustrates a cross section view of the step motor similar to the one in FIG. 9A. In this exemplary embodiment, only parallel to substrate 10 plane layers of piezoelectric stack actuators are fabricated. Substrate 10, needle 920, via 930 and piezoelectric stack actuators 917 and 919 (as well as the not shown in the figure, piezoelectric stack actuators 916 and 918) are the same as in FIG. 9B. Piezoelectric stack actuators 912 and 914 (as well as the not shown in the figure, piezoelectric stack actuators 911 and 913) are replaced by piezoelectric stack actuators 912a and 914a (as well as the not shown in the figure, piezoelectric stack actuators 911a and 913a). Piezoelectric stack actuators 911a, 912a, 913a, and 914a are constructed from 6 layers (tiles) that are also parallel to substrate 10 plane. The voltage to the electrodes of the top six piezoelectric layers are driven independently from the voltage to the electrode of the bottom four piezoelectric layers. In order to enable the grip, the polarization of the top six piezoelectric layers, i.e., piezoelectric stack actuators 911a, 912a, 913a, and 914a, is parallel to substrate 10 plane and perpendicular to the electric field created by the electrodes as illustrated by the vector P=→. When applying voltage on the electrodes of actuators 911a, 912a, 913a, and 914a, the piezoelectric stack actuators will tilt towards needle 920 and perform the grip of the needle. This tilt operation is illustrated in the figure for piezoelectric stack actuators 914a. The polarization of the bottom four piezoelectric layers of piezoelectric stack actuators 911, 912, 913 and 914 is perpendicular to substrate 10 plane so that these actuators are performing upwards and downwards movement as in the embodiment of FIG. 9B. Setting the polarization of the piezoelectric layers is done by process called poling. This process can only be carried out at temperatures below a temperature called Curie temperature. The process of poling involves aligning all of these individual dipole moments, so that they all point in the same general direction. This is accomplished by putting the piezoelectric material in a constant electric field to force the dipoles to align. This is done by driving the electrode with voltage that is higher than normal voltage of operation. In the presence of this higher electric field each dipole will feel a torque if it is not parallel to the field lines produced, and so is turned to the direction of the electric field. When the electric field is removed, the dipoles remain fairly aligned, although there will still be some element of random direction.

Figure 9D:
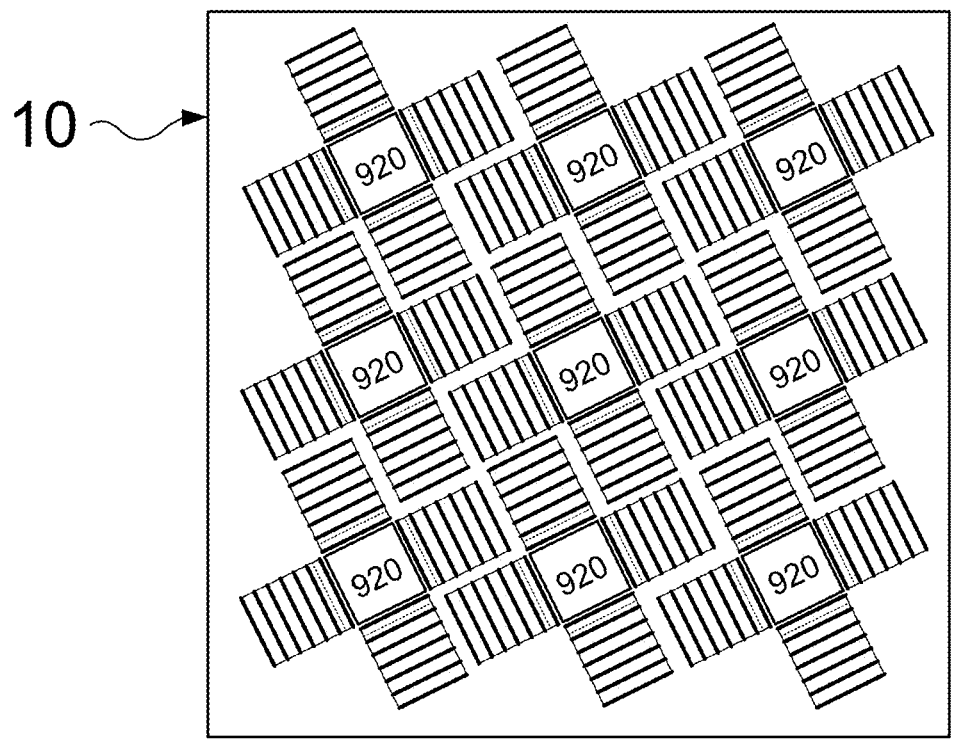

Reference is now made to FIG. 9D. FIG. 9D illustrates a top view of a 2D needle array embodiment using the embodiments of FIG. 9B or FIG. 9C. Substrate 10 is paved with a plurality of needles 920 in 2D array shape. Each needle 920 has its own step motor. In such a way hundreds, thousands and up to millions of micro needles can be fabricated on a single chip.

Cantilever Implementation

As seen above a piezoelectric stack actuator is one solution to overcome the small displacement of a bulk piezoelectric crystal. Another solution is to use piezoelectric cantilevers. FIGS. 10A-10C and FIGS. 10D-10F show two types of piezoelectric cantilevers.

Reference is now made to FIGS. 10A-10C. FIGS. 10A-10C illustrate a version of cantilever 310 bending perpendicular to substrate plane, while FIGS. 10D-10F illustrate a version of cantilever 360 bending parallel to substrate plane. FIG. 10A is a top view of cantilever 310. cantilever 310 is built on top of substrate 10. From top view only electrode 315 is visible. FIG. 10B is a side view of cantilever 310. Cantilever 310 is fabricated over anchor 316 that is connected to substrate 10. Cantilever 310 has five layers: bottom electrode 311, bottom piezoelectric layer 312, center (common) electrode 313, top piezoelectric layer 314, and top electrode 315. The polarization of the piezoelectric layers 312 and 314 is perpendicular to substrate 10 plane. FIG. 10C is a side view of cantilever 360. In FIG. 10C, the dynamic bending movements, when an electric signal is driven to the cantilever actuator, is illustrated. Cantilever 310 bends downward toward substrate 10 or upwards against substrate 10.

Reference is now made to FIGS. 10D-10F. FIG. 10D is a top view of cantilever 360. cantilever 360 is built on top of substrate 10. From top view only electrode 364 and 365 are visible. FIG. 10E is a side view of cantilever 360. Cantilever 360 is fabricated over anchor 366 that is connected to substrate 10. Cantilever 360 has three layers: bottom electrodes 361 and 362, piezoelectric layer 363, and top electrodes 364 and 365. The polarization of the piezoelectric layer 363 are perpendicular to substrate 10 plane. FIG. 10F is a top view of cantilever 360. In FIG. 10F the dynamic bending when electric signal is driven to the cantilever actuator is illustrated. Cantilever 360 bends in parallel to substrate 10 plane. In bending mode, if the voltage between electrodes 361 and 364 is positive, the voltage between electrode 362 and 365 is negative. This driving voltage causes one side of the cantilever to contract while causing the other side to expand and consequently the cantilever bends. In an exemplary embodiment of the invention, electrodes 361 and 362 are connected together or fabricated as a single electrode and become a common electrode, Alternatively, electrodes 364 and 365 are connected together or fabricated as a single electrode and become a common electrode.

In Plane Cantilever Embodiments

Figure 11A:
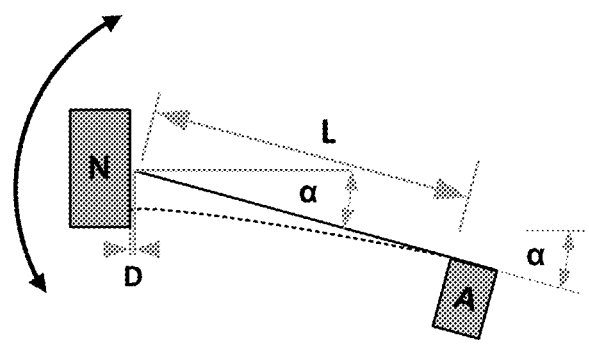
FIG. 11A-FIG. 11B are illustrations of bending geometry for in-plane cantilevers actuators in accordance with some embodiment of the present invention.
Figure 11B:
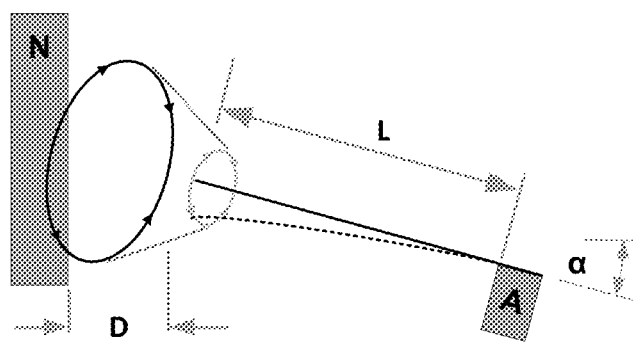

Reference is now made to FIGS. 11A-11B. FIGS. 11A-11B illustrate in plane cantilever embodiments. FIG. 11A is a top conceptual view of the basic cantilever illustrated in FIGS. 10D-10F. In rest state, the cantilever is straight (i.e., not bent) with angle α relative to a perpendicular line of surface of the needle (illustrated in the figure by the box in the left indicated by N). The angle α of the cantilever is formed by the anchor orientation (illustrated in the figure by the box tilted by angle α in the right and indicated by the letter A). The anchor is connected to the substrate (not shown in the figure). In rest state the distance between the tip of the cantilever and the needle surface is D. The length of the cantilever is L. The angle, a, and the maximum displacement of the cantilever during activation, determines if the maximum displacement in bending will closes the gap D and enables the cantilever to contact the needle and activate force on the needle surface. If fabrication limitation dictate larger gap D, the length of the cantilever may be increased to meet this fabrication requirement.

In FIG. 11B a top view of the same cantilever as in FIG. 10A is illustrated. The electrodes of the cantilever in this illustration are driven by two sine waves signals with a phase difference to induce an elliptical movement of the cantilever tip. In this case, in part of the elliptical path, the cantilever tip gets into contact with the needle and pushes it downwards as illustrated by the needle object and the elliptical path (enlarged) on the left of the figure. The tip of the cantilever does not actually enter into the needle, rather bent on the needle surface to complete the circular movement. Carful implementation of the geometry and the driven signals enables efficient continuous movement of the needle as long as the cantilever is driven to create the elliptical movement. In an exemplary embodiment of the invention, the sine wave signals are driven in the resonance frequency of the cantilever.

Reference is now made to FIGS. 12A-12D. FIG. 12A illustrates a top view of a step motor 450. Step motor 450 comprises four piezoelectric cantilevers 452, 544, 546 and 548. Piezoelectric cantilevers 452, 544, 546 and 548 are connected to a substrate (not shown in the figure) through anchors 412 and 413. The dashed line represent the activated tilted state of the piezoelectric cantilever. To lock needle 420 to its position all piezoelectric cantilevers 452, 544, 546 and 548 bend to press needle 420 from all directions, piezoelectric cantilever 452 press downwards and leftwards, piezoelectric cantilever 454 press upwards and leftwards, piezoelectric cantilever 456 press upwards and rightwards, and piezoelectric cantilever 458 press downwards and rightwards. The total equivalent force that all the cantilevers are inducing on needle 420 is zero so the needle is in lock state. To move the needle downwards piezoelectric cantilevers 454 and 456 are released, so now the needle is forced by piezoelectric cantilevers 452 and 458 to move downwards. Cantilevers 452 and 458 now release and grip again simultaneously with cantilevers 454 and 456 to lock the needle in its incremental step downwards. Moving needle 420 upwards is done similarly with the obvious modification in piezoelectric cantilevers 452, 452, 456 and 458 activation sequence; In an exemplary embodiment of the invention, piezoelectric cantilevers 452, 454, 456 and 458 perform synchronized elliptical movement to move the needle downwards or upwards. In moving needle 420 downwards, piezoelectric cantilevers 452, 454 elliptically rotate counter-clock-wise and piezoelectric cantilevers 456, 458 rotate clock-wise. In moving needle 420 upwards, piezoelectric cantilevers 452, 454 elliptically rotate clock-wise and piezoelectric cantilevers 456, 458 elliptically rotate counter-clock-wise.

Reference is now made to FIG. 12B. FIG. 12B is a top view illustration of another step motor 460. Step motor 460 comprises four piezoelectric cantilevers 462, 464, 466 and 468. The design is almost identical to step motor 450 but the cantilevers orientations are in different angle order. Piezoelectric cantilevers 462, 464, 466 and 468 are connected to a substrate (not shown in the figure) through anchors 414 and 415. The sequence to move needle 450 is similar to the one described hereinabove.

Reference is now made to FIG. 12C. FIG. 12C illustrates a top view of yet another step motor 470. Step motor 470 comprises eight piezoelectric cantilevers 471, 472, 473, 474, 475, 476, 477 and 478. Piezoelectric cantilevers 471-478 are connected to a substrate (not shown in the figure) through anchors 416 and 417. Each anchor, 416 or 417 in this embodiment, support four piezoelectric cantilevers. The additional four piezoelectric cantilevers relative to the step motor embodiment of FIG. 12A gives the step motor additional power, and in addition enables the step motor to control better needle backlash situations that are more likely to occur in four piezoelectric cantilevers arrangements. The sequence of moving the needle in this embodiment has more options but basically use the same principles as described hereinabove for the other embodiment.

Reference is now made to FIG. 12D. FIG. 12D illustrates a top view of another step motor 480. Step motor 480 combines in a compact way two step motors that are illustrated in FIG. 12A with one step motor that is illustrated in FIG. 12B. Step motor 480 has six anchors 418 supporting twelve piezoelectric cantilevers 485. In an exemplary embodiment of the invention, a plurality of step motors 450 and 460 are fabricated along needle 420 to create a compact multi-cantilever step motor.

Out of Plane Piezoelectric Cantilever Embodiments

The use of piezoelectric cantilevers as a basic element of a step motor can be used when the needle movement is out of plane too as presented herein below.

Figure 13A:
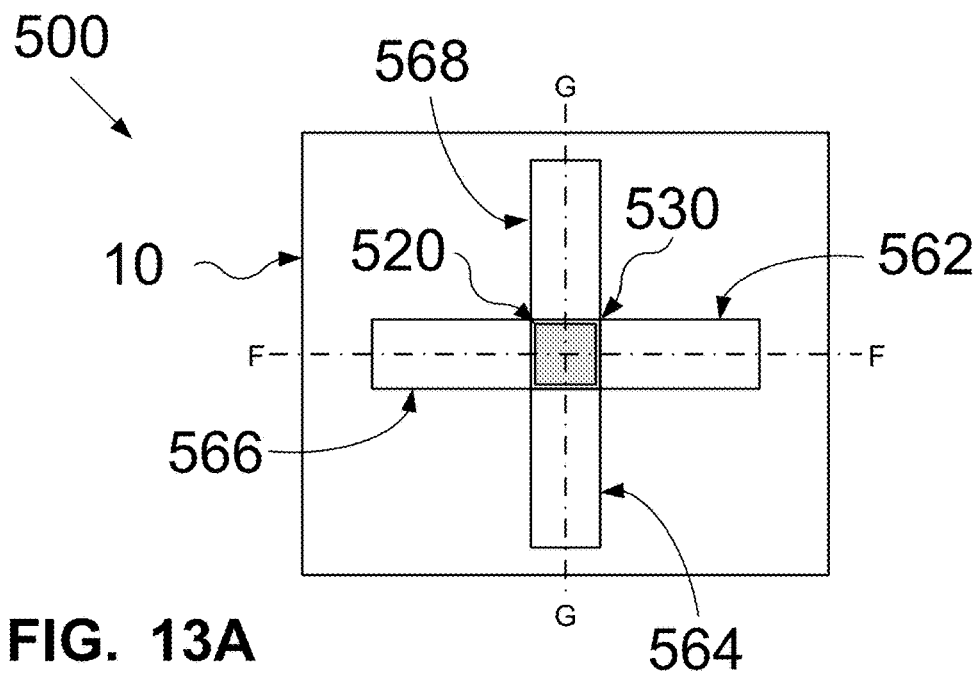
FIG. 13A-FIG. 13C are illustrations of out-of-plane needle movement step motor comprising piezoelectric cantilever actuators.

Reference is now made to FIGS. 13A-11C. FIGS. 11A-11B illustrate out of plane step motor embodiments. FIG.

Figure 13B:
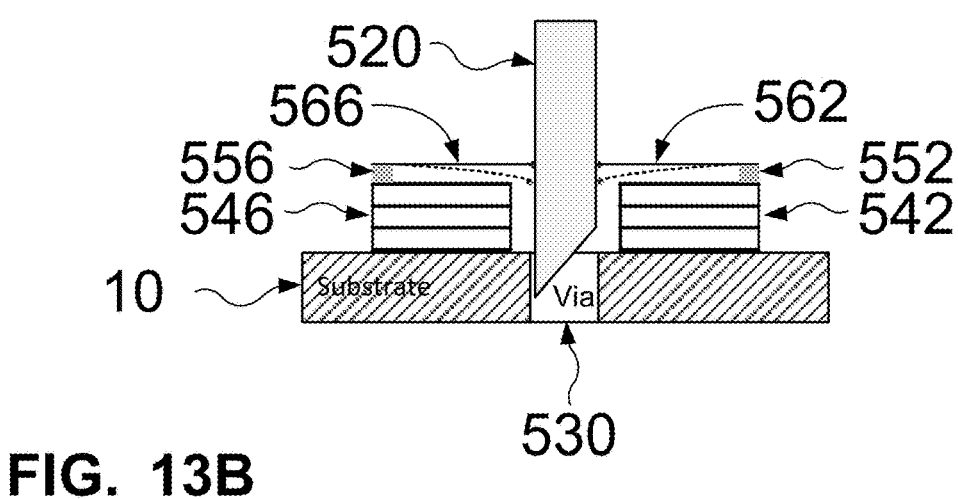
Figure 13C:
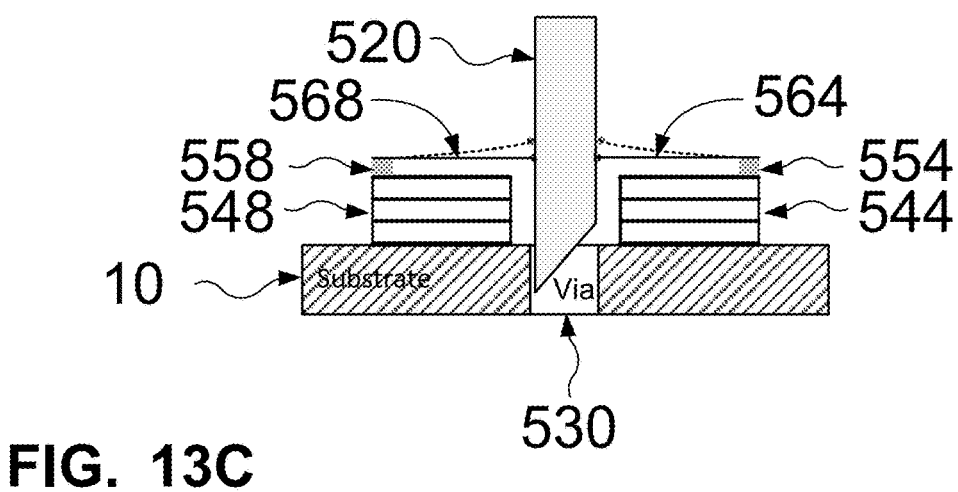

13A is a top view of a step motor 500. A substrate 10 has via 530 and a needle 520 configured to pass through via 530. From the top view for piezoelectric cantilevers 562, 564, 566 and 568 are visible. FIG. 13B is a cross-sectional view across line F-F and FIG. 13C is a top section view across line G-G, Reference is now made to FIG. 13B. FIG. 13B is a cross-sectional view across line F-F of step motor 500. In the figure, on top of substrate 10 having via 530 there are two piezoelectric stack actuators 542 and 546. Piezoelectric stack actuators 542 and 546 are similar to piezoelectric stack actuators 917 and 919 illustrated in FIG. 9B. Piezoelectric stack actuators 542 and 546 are able to contract and expand so anything fabricated on top can move upwards or downwards relative to substrate 10. On top of piezoelectric stack actuators 542 and 546 isolator layers 552 and 556 are fabricated respectively. On top of isolator layers 552 and 556 piezoelectric cantilevers 562 and 566 are fabricated. Piezoelectric cantilevers 562 and 566 are similar to piezoelectric cantilever 310 illustrated in FIG. 10A-10C and they can bend upwards or downwards relative to substrate 10. Piezoelectric stack actuators 542 and 546 and piezoelectric cantilevers 562 and 566 are fabricated with in-plane piezoelectric layer, i.e. the piezoelectric layers are stacked on each other in parallel with the substrate plane. When needle 520 is inserted to via 530 piezoelectric cantilevers 562 and 566 are activated and bent downwards to allow needle 520 insertion. When the piezoelectric cantilevers 562 and 566 are deactivated, piezoelectric cantilevers 562 and 566 bend back to straight rest position and grip needle 520.

Reference is now made to FIG. 13B. FIG. 13B is a cross-sectional view across line F-F of step motor 500. In the figure, on top of substrate 10 having via 530 there are two piezoelectric stack actuators 544 and 548. Piezoelectric stack actuators 544 and 548 are similar to piezoelectric stack actuators 917 and 919 illustrated in FIG. 9B. Piezoelectric stack actuators 544 and 548 are able to contract and expand so anything fabricated on top can move upwards or downwards relative to substrate 10. On top of piezoelectric stack actuators 544 and 548, isolator layers 554 and 558 are fabricated respectively. On top of isolator layers 554 and 558 piezoelectric cantilevers 564 and 568 are fabricated. Piezoelectric cantilevers 564 and 568 are similar to piezoelectric cantilever 310 illustrated in FIG. 10A-10C and they can bend upwards or downwards relative to substrate 10. Piezoelectric stack actuators 544 and 548 and piezoelectric cantilevers 564 and 568 are fabricated with in plane piezoelectric layer, i.e. the piezoelectric layers are stacked on each other in parallel with the substrate plane. When needle 520 is inserted to via 530 piezoelectric cantilevers 564 and 568 are activated and bent upwards to allow needle 520 insertion. Note that during needle 520 insertion piezoelectric cantilevers 562 and 566 are bent downwards and piezoelectric cantilevers 564 and 568 are bent upwards. When the piezoelectric cantilevers 564 and 568 are deactivated, piezoelectric cantilevers 564 and 568 are bent back to straight rest position and grip needle 520.

In rest needle is gripped by two cantilevers that press the needle upwards and two cantilever that press the needle downwards. During needle movement downwards piezoelectric cantilevers 564 and 568 grip the needle and piezoelectric cantilevers 562 and 566 release the needle and piezoelectric stack actuators 544 and 548 contract. During needle movement upwards piezoelectric cantilevers 562 and 566 grip the needle and piezoelectric cantilevers 564 and 568 release the needle and piezoelectric stack actuators 542 and 546 expand.

The ability to apply opposite voltage to each pair of cantilevers allows a pair of cantilever to bend upwards and the other pair of cantilever to bend downwards in order to allow holding the needle for both upwards and downwards movements. After needle insertion, when voltage supply is stopped and the cantilevers return to non-bent state they are effectively trying to bend back to a straight state but due to the fact that the cantilevers are fabricate a bit longer, the cantilever contact needle 520 and stay a bit bent and grips the needle. Needle 520 is kept gripped without any need for energy supply.

In Plane Mixed Piezoelectric Stack Actuators and Cantilever Embodiment

Figure 14:
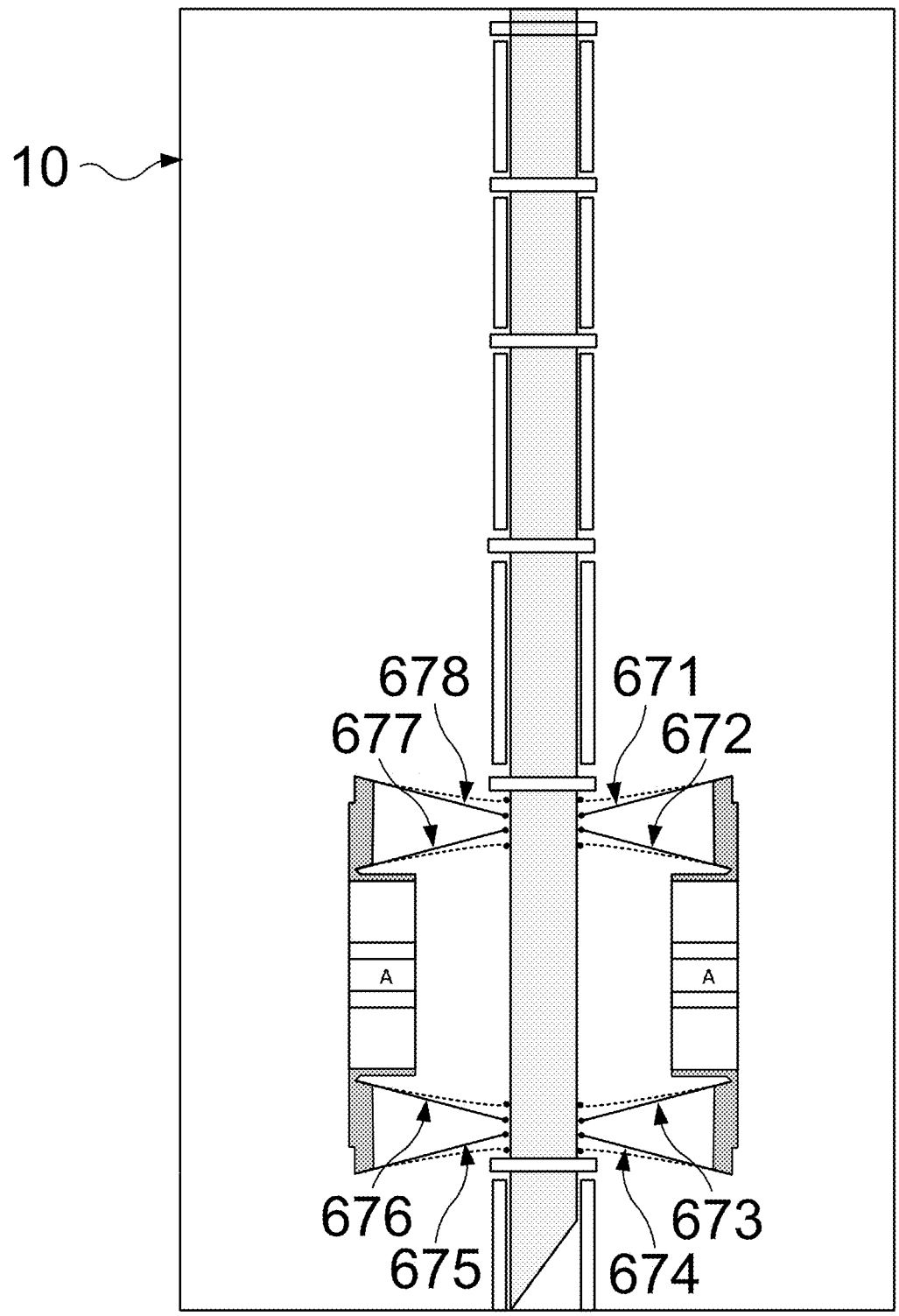
FIG. 14 is an illustration of a step motor comprises both piezoelectric stack actuators and piezoelectric cantilever actuators in accordance with an embodiment of the present invention.

Reference is now made to FIG. 14. FIG. 14 illustrates a die 600 comprising a step motor and a needle that is similar to the die illustrated in FIG. 8B. The only change in this embodiment is that the four stack actuators 813, 814, 817 and 818 that are used to grip the needle are replaced with eight piezoelectric cantilevers 671, 672, 673, 674, 675, 676, 677 and 678 that are similar to the cantilevers illustrated in FIG. 12C. However, in this case, cantilever 671-678 are used just for gripping the needle while the movement of the needle is done by contracting or expanding the piezoelectric stack actuators.

To summarize the embodiments described above, the needle system that was described or the apparatus for piercing an object is comprising: -(a) one or more needles; and (b) one or more actuators comprising at least one of or any combination of: (1) one or more piezoelectric stack actuators and (2) one or more piezoelectric cantilever actuators. The actuators form a plurality of arms that are configured to grip the one or more needles. The needles are configured to pierce the object. The piezoelectric actuators are configured to expand, contract or bend. The arms are configured to dynamically hold or release the grip from the needles by expanding, contracting or bending some of the plurality of the piezoelectric actuators. The arms that are holding the needles are configured to move the needles by expanding, contracting or bending some of the plurality of the piezoelectric actuators.

Fabrication Process

The method of fabricating of an apparatus for piercing an object that comprises the substrate, one or more needles, one or more anchors and one or more piezoelectric actuators that can be at least one of or any combination of (1) bulk piezoelectric crystals (2) piezoelectric stack actuators as described in FIG. 6-FIG. 9, (3) piezoelectric cantilever actuator as describe in FIG. 10-FIG. 14, is given hereinafter.

The fabrication method involve the steps of:
(1) depositing sacrificial layer over the substrate;
(2) depositing conducting layer over the sacrificial layer;
(3) depositing piezoelectric layer over the conducting layer;
(4) etching a geometry of one or more piezoelectric actuators using a first mask created by lithography process;
(5) depositing one or more needle and one or more anchors using a second mask created by lithography process and a lift-off process; and
(6) etching the sacrificial layer under the needle and the one or more piezoelectric actuators.

This process is for fabricating a piercing apparatus wherein the anchors are configured to connect the substrate to the piezoelectric actuators and one or more piezoelectric actuators are configured to move the one or more needles.

Alternatively, the step of deposition of the sacrificial layer may be omitted and instead etching of the top surface of the substrate may be done using SCREAM process. The etching of top surface of the substrate is done under the needle and the one or more piezoelectric actuators. First, a vertical anisotropic dry etching of pattern of pores is performed. Second, etching horizontal extension of the pores using wet or gas etching, is performed.

Figure 15A:
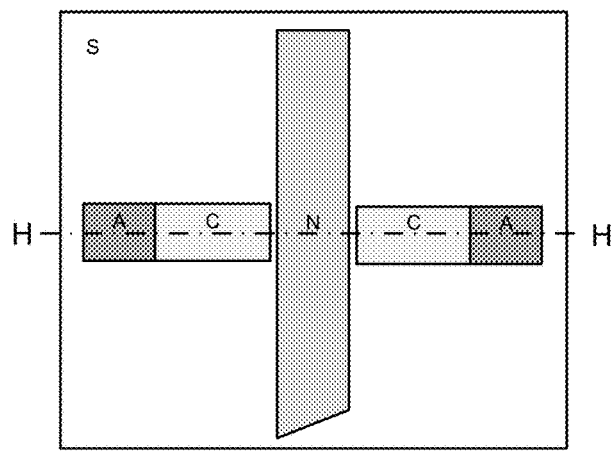
FIG. 15A-FIG. 15L are illustrations of the process to fabricate an exemplary piercing apparatus in accordance with some embodiments of the present invention.

To describe the fabrication process in more details, we take, for example, the step motor embodiment of FIG. 12A. To simplify the process explanation, we rotate the cantilevers so it will be easier to explain the fabrication process in a single step by step cross-sectional views. The top view of the conceptual modified design is given in FIG. 15A. FIG. 15A illustrates a substrate, indicated by S, two anchors, indicated by A, a needle, indicated by N, and two piezoelectric cantilevers with top and bottom electrodes indicated by C. The fabrication process will be illustrated by cross sectional views across line H-H.

Figure 15B:
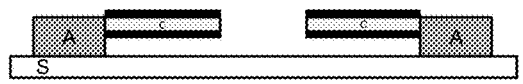

Reference is now made to FIG. 15B. FIG. 15B illustrate a cross sectional view of the desired final stage of fabrication. In the final stage only anchors A are connected to substrate S. the piezoelectric cantilevers C are connected to anchors A. On top and below the piezoelectric material of cantilever C there are metal electrodes (in black in the figure). The needle is free from substrate S and held by the cantilevers C.

Figure 15C:
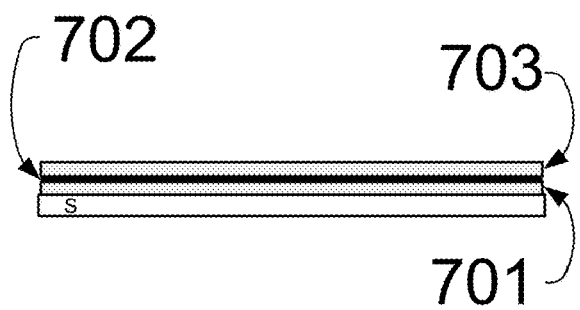

Reference is now made to FIG. 15C. FIG. 15C illustrate the first stage of fabrication. In this stage the substrate S, typically come in the shape of a round wafer, is covered with three layers: the first layer is sacrificial layer 701, typically made of silicon oxide (SOX). The second layer 702 is a conducting layer, e.g., metal layer. The third layer 703 is a piezoelectric layer, e.g., made from PZT material. Piezoelectric layer 703 is sintered and polled to have crystal polarization perpendicular to the substrate plane in this stage. Typically a plurality of chips are made from a single wafers and the processes that are herein below are done simultaneously to a plurality of chips or dies on the wafer and the chips are cut off to separate chips in the final stage.

Figure 15D:
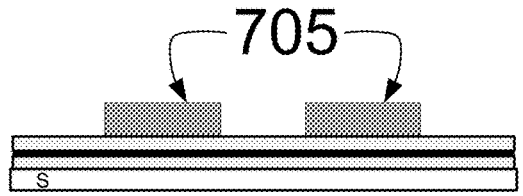

Reference is now made to FIG. 15D. FIG. 15D is the second stage of fabrication. In this stage photoresist material is deposited on the wafers, a mask with a geometric 2D pattern is made, a photolithography followed be a development process and clearing of the developed photo resist, hereinafter lithography stage, performed and the final 2D photo resist 705 mask is deployed over the wafer. The 2D pattern, in this case, is the pattern that form the cantilevers.

Figure 15E:
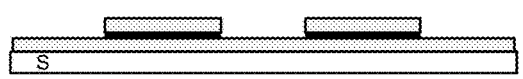

Reference is now made to FIG. 15E. FIG. 15E is the third stage of the fabrication. Using the photoresist mask the areas that are not part of the cantilevers are etched away, The etching is stopped at the sacrificial layer that is not sensitive to the specific agent used in this etching process.

Figure 15F:

Reference is now made to FIG. 15F. FIG. 15F is the fourth stage of the fabrication. Another thick photoresist layer is spread over the wafer. This layer of photoresist covers the existing cantilever pattern.

Figure 15G:
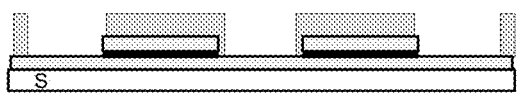

Reference is now made to FIG. 15G. FIG. 15G is the fifth stage of the fabrication. In this stage another lithography process is made to expose the area to fabricate the needle and the anchors.

Figure 15H:
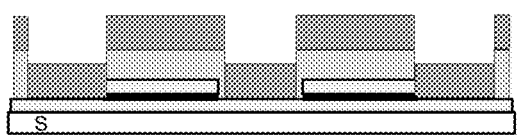

Reference is now made to FIG. 15H. FIG. 15H is the sixth stage of the fabrication. In this stage the needle and the anchors are fabricated in a process called deposition. Since the deposition is done over the mask part of the material of this layer is deposited over the sacrificial layer while other part of the material of this layer are deposited over the photoresist mask.

Figure 15I:
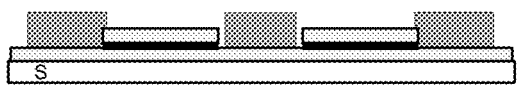

Reference is now made to FIG. 15I. FIG. 15I is the seventh stage of the fabrication. In this stage we clean the photoresist layer so every material of the layer that was over the photoresist layer is cleared away too. This process is known in the art as lift-off process.

Figure 15J:
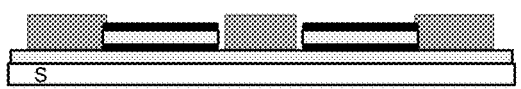

Reference is now made to FIG. 15J. FIG. 15J is the eighth stage of the fabrication. In this stage, a deposition of the top electrodes and metal connections is performed. This process involves a lithography and metal deposition and, optionally, one or more isolator layers and additional metal layers.

Figure 15K:
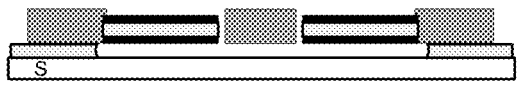

Reference is now made to FIG. 15K. FIG. 15K is the ninth stage of the fabrication. In this stage etching the sacrificial layer is done. This stage will free the needle and cantilever from the actuator. Etching is done through the opening in on the edges of the needles and actuator (the openings cannot be seen clearly on the cross sectional view but are more noticeable in 3D top view). The area under the anchor is partially etched away too. Since the anchor area is wide and aching time is controlled, a significant area under the anchor is not etched to and allow the anchoring function of the anchor.

At this stage we have a chip functionally similar to the desired one represented in FIG. 15B. After this stage additional stages such as cutting the wafer to die and packaging is performed.

Figure 15L:

Reference is now made to FIG. 15L. FIG. 15L is an alternative process that uses the substrate as the sacrificial layer. All steps are similar to the above but the last etching is done over the substrate with a process known as SCREAM. In SCREAM process the etch is done using pattern of pores on the area that we going to etch the substrate. The etching begins with anisotropic dry etching to penetrate vertically the silicon substrate with the specific pore pattern then extend the etching horizontally by isotropic wet/gas phase etching. The cross section of this process after the SCREAM process is illustrated in FIG. 15L.

The above described fabrication process comprises only the conceptual major process stages and many other steps and stages are involved in each stage and between steps. The order of some steps may be changed and it is evident that many alternatives, modifications and variations will be apparent to those skilled in the art.

Deposition steps may be done by various types of chemical vapor deposition (CVD), evaporation, sputtering, physical vapor deposition (PVD), Atomic layer deposition (ALD), electrochemical deposition (ECD), and the like. Etching may be dry etching, atomic layer etching (ALE), Wet etching, Plasma etching, and the like. Other process may include thermal treatments, Chemical-mechanical polishing (CMP) and the like.

Needle Friction

The discussion about the ways to reduce the needle friction have been discussed in details in U.S. patent application Ser. No. 15/296,068 which is incorporated by reference. Another option to reduce friction, is to keep the needle on the air at all time by the actuators as illustrated in FIG. 7. One way to do that is to fabricate the actuators in initial grip state by exploiting the build-in tension of material during fabrication. During etching the sacrificial layer the actuator are deformed to hold the needle so that when the needle is released afterwards it is already gripped by the actuators. Another way is to hold the needle with a plurality of small snaps that are torn when the apparatus is connected to power. When the power to the apparatus is delivered, the first act is to grip the needle with the actuator. Then the snaps are torn by first moving the needle or alternatively by burning the snaps using a current flow (like in fuse burn operation). In this exemplary embodiment of using snaps, the needle is always held with air gap from the substrate and the friction with the substrate is illuminated.

It is expected that during the life of a patent maturing from this application many relevant applications will be developed and the scope of the implementation is intended to include all such new technologies a priori.

The terms "comprises", "comprising", "includes", "including", "having" and their conjugates mean "including but not limited to".

The term "consisting of means "including and limited to".

As used herein, the singular form "a", "an" and "the" include plural references unless the context clearly dictates otherwise. For example, the term "an element" or "at least one element" may include a plurality of elements, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An apparatus for piercing an object comprising:
   (a) one or more needles; and
   (b) one or more piezoelectric actuators comprising a at least one of or any combination of one or more piezoelectric stack actuators and one or more piezoelectric cantilever actuators, wherein:
      (1) the one or more piezoelectric actuators form a plurality of arms that are configured to grip the one or more needles;
      (2) the one or more needles are configured to pierce the object;
      (3) the one or more piezoelectric actuators are configured to expand, contract or bend;
      (4) each pair of the plurality the arms are configured to dynamically hold or release the grip from the one or more needles by expanding, contracting or bending some of the one or more of the piezoelectric actuators; and
      (5) when some of said arms hold the one or more needles, these holding arms are configured to move the one or more needles by expanding, contracting or bending some of the one or more of the piezoelectric actuators.

2. The apparatus of claim 1, wherein the apparatus further comprising a one or more drivers configured to activate the one or more piezoelectric actuators and a controller configured to control the one or more drivers.

3. The apparatus of claim 1, wherein the apparatus comprising first four piezoelectric stack actuators configured to grip any of the one or more needles and second four piezoelectric stack actuators configured to move said first four piezoelectric stack actuators.

4. The apparatus of claim 1, wherein the one or more piezoelectric cantilever actuator performs at least one of bending movement or elliptic movement.

5. The apparatus of claim 1, wherein said one or more needles have mechanical support to hold any one of the one or more needles and to allow sliding only to a desired direction.

6. The apparatus of claim 1, wherein said object is a human organ and the one or more needles are used for hypodermal treatment.

7. The apparatus of claim 1, wherein said object is an article of manufacturing and the apparatus is used for manipulating or piercing the object during the process of the manufacturing.

8. The apparatus of claim 1, wherein said object is a lab object under test or a biological organ and the apparatus is used for testing or measuring or manipulating the lab object under test or the biological organ.

9. The apparatus of claim 1, wherein the apparatus is fabricated over a substrate, and the substrate is connected to the one or more piezoelectric actuators by one or more anchors.

10. The apparatus of claim 1, wherein the apparatus is a chip fabricated in semiconductor foundry by semiconductor fabrication processes.

11. The apparatus of claim 1, wherein the apparatus comprises layers that are fabricated on top of a substrate.

12. The apparatus of claim 11, wherein a sacrificial layer is deposit over the substrate, and wherein parts of the sacrificial layer are etched afterwards during a fabrication process.

13. The apparatus of claim 11, wherein layers of at least one of or any combination of (a) conducting materials, (b) piezoelectric materials, and (c) electric isolation materials, are deposit over the suberate or over another layer.

14. The apparatus of claim 9, wherein a fabrication process of the apparatus comprises the steps of:
   (1) deposit a sacrificial layer over the substrate;
   (2) deposit a conducting layer over the sacrificial layer;
   (3) deposit a piezoelectric layer over the conducting layer;
   (4) etch a geometry of the one or more piezoelectric actuators using a first mask created by a first lithography process;
   (5) deposit the one or more needles and the one or more anchors using a second mask created by a second lithography process and a lift-off process; and
   (6) etch the sacrificial layer under the needle and the one or more piezoelectric actuators.

15. The apparatus of claim 9, wherein a fabrication process of the apparatus comprises the steps of:
   (1) deposit a conducting layer over the substrate;
   (2) deposit a piezoelectric layer over the conducting layer;
   (3) etch a geometry of the one or more piezoelectric actuator using a first mask created by lithography process;
   (4) deposit the one or more needles and the one or more anchors using a second mask created by a lithography process and a lift-off process; and
   (5) etch the top surface of the substrate under the one or more needles and the one or more piezoelectric actuators using a two stage SCREAM etching process comprising: first, vertical anisotropic dry etching of pattern of pores, and second, horizontal extension of the pores etching using wet or gas etching.

16. The apparatus of claim 10, wherein the chip comprises one or more through-chip via filled with conducting material and configured to provide a connection with another chip using wafer bonding fabrication process.

17. The apparatus of claim 11, wherein a fabrication process of the apparatus comprises a step of depositing multilayers of piezoelectric materials interleaved with layers of conducting materials.

18. The apparatus of claim 11, wherein a fabrication process of the apparatus comprises a step of depositing tiles of piezoelectric materials interleaved with tiles of conducting materials using two masks lithography and liftoff processes.

19. The apparatus of claim 10, wherein the chip comprises a 1 D array of needles moving in-plane.

20. The apparatus of claim 10, wherein the chip comprises a 2 D array of needles moving out-of-plane.

* * * * *